United States Patent [19]

Yamada et al.

[11] Patent Number: 5,149,702
[45] Date of Patent: Sep. 22, 1992

[54] CYCLOHEPTENOPYRIDINE DERIVATIVES, PROCESS FOR PREPARATION THEREOF AND ANTIULCER AGENTS CONTAINING THE SAME

[75] Inventors: Shin-ichi Yamada, Fukushima; Takao Goto, Koori; Rie Yorita, Fukushima; Eizi Shimanuki, Fukushima; Takaji Yamaguchi, Fukushima; Kentaro Kogi, Shiroishi; Senichi Narita, Tokyo, all of Japan

[73] Assignee: Toa Eiyo Ltd., Tokyo, Japan

[21] Appl. No.: 618,943

[22] Filed: Nov. 27, 1990

[51] Int. Cl.⁵ .............................. A61K 31/44
[52] U.S. Cl. .................. 514/303; 514/235.2; 514/299; 514/926; 514/927; 544/127; 546/112; 546/118; 546/183
[58] Field of Search ............ 548/327; 514/395, 299, 514/303, 235.2, 926, 927; 546/183, 112, 118; 544/127

[56] References Cited

U.S. PATENT DOCUMENTS

| | | | |
|---|---|---|---|
| 4,045,563 | 8/1977 | Berntsson et al. | 548/327 |
| 4,563,455 | 1/1986 | Ueda et al. | 548/327 |
| 4,735,955 | 4/1988 | Tomiyama et al. | 548/327 |
| 4,738,970 | 4/1988 | Uchida et al. | 546/153 |
| 4,767,769 | 8/1988 | Hockley et al. | 514/395 |
| 4,824,856 | 4/1989 | Okabe et al. | 514/395 |
| 4,880,815 | 11/1989 | Uchida et al. | 546/118 |

FOREIGN PATENT DOCUMENTS

2171995 9/1986 United Kingdom .

OTHER PUBLICATIONS

Uchida et al., *Chem. Pharm. Bull.*, 37(6), pp. 1517–1523, (1989), (Chem. Abs. only).

Primary Examiner—Carolyn Elmore
Assistant Examiner—Scott C. Rand
Attorney, Agent, or Firm—Wenderoth, Lind & Ponack

[57] ABSTRACT

Provided are cycloheptenopyridine derivatives represented by the general formula

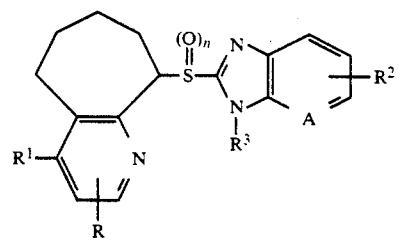

[I]

[wherein R represents a hydrogen atom or lower alkyl group; $R^1$ represents a hydrogen atom, halogen atom, lower cycloalkoxy group, amido group, substituted phenoxy group, substituted benzyloxy group, lower alkoxy group optionally containing halogen atoms(s), nitro group, hydroxyl group, lower alkenyloxy group, lower alkylthio group, or a group—$NR^4R^5$ (wherein $R^4$ and $R^5$ may be the same or different and each represent a hydrogen atom or lower alkyl group, or $R^4$ and $R^5$ mutually combine together with the nitrogen atom adjacent thereto to form a 5- or 6-membered heterocyclic group); $R^2$ represents a hydrogen atom, halogen atom, lower alkyl group optionally containing a halogen atom, lower alkoxy group optionally containing a halogen atom, hydroxyl group, acyl group, lower alkoxycarbonyl group, nitro group or amino group; $R^3$ represents a hydrogen atom, a lower alkyl group, lower alkoxymethyl group, lower alkylcarbonyl group, lower alkoxycarbonyl group, carbamoyl group, lower alkylcarbamoyl group, lower alkylcarbonylmethyl group, lower alkoxycarbonyl group, lower acyloxymethyl group, lower alkylsulfonyl group, or physiologically acceptable protective group eliminatable in an acid medium or under a physiological condition; n represents 0 or 1; and A represents a methine carbon or nitrogen atom] or their salts. These derivatives and their salts are useful as antiulcer agents.

2 Claims, No Drawings

CYCLOHEPTENOPYRIDINE DERIVATIVES, PROCESS FOR PREPARATION THEREOF AND ANTIULCER AGENTS CONTAINING THE SAME

This invention relates to novel cycloheptenopyridine derivatives useful as treatment agents for gastric or duodenal ulcer.

As for recent pathophysiological studies of gastric or duodenal ulcer, the behavior of potassium ion-dependent adenosine triphosphatase (hereinafter abbreviated as $(H^+ + K^+)$ ATPase), which is involved in hydrochloric acid production in the gastric endoplasmic reticulum, vehicle has drawn attention, and the presence or absence of inhibitory activity of this enzyme has come to be used as an indicator for antiulcer agents (Gastroenterology vol. 1, 420, 1943 and ibid vol. 73, 921, 1977). It was revealed that this enzyme is located on parietal cells of the gastric mucosa and plays a role of a key enzyme of gastric proton pump, and blockade of this enzyme may be useful to suppress gastric acid secretion. At present, as typical examples of antiulcer agents which exhibit selective inhibitory action against this $(H^+ + K^+)$ ATPase and are under development, there can be mentioned benzimidazole derivatives such as omeprazole having an unsubstituted or trisubstituted pyridylmethylsulfinyl group at the side chain (Japanse Laid-Open Patent Publication No. 141783/1979) and NC-1300 having an alkylaminophenylmethylsulfinyl group at the side chain (Japanese Laid-Open Patent Publication No. 60660/1986). Further, it has been known that some of the benzimidazole derivatives have a protecting activity for gastrointestinal mucosal cell (Japanese Laid-Open Patent Publication No. 53406/1982).

Histamine $H_2$ receptor antagonists represented by cimetidine exhibit excellent healing effect on peptic ulcer because they have a potent inhibitory action on gastric acid secretion. However, it is the present state of things that these drugs cannot simply be concluded to be satisfactory drugs because when administration thereof is discontinued due to complete healing, reccurrence of ulcer is often observed, and that known $(H^+ + K^+)$ ATPase inhibitors represented by omeprazole have a problem on stability and, therefore, their improvements are being desired. Further, peptic ulcers are generally thought to result from an imbalance between the aggressive factors such as hydrochloric acid and pepsin and the defensive factors of the tunic mucosa side such as mucous secretion and mucosal bloodstream, and thus drugs having an inhibitory action on a gastric acid secretion and a cytoprotection together are being desired.

The present inventors vigorously studied to develop antiulcer agents which have a potent inhibitory action on gastric acid secretion and a cytoprotection together, and are physiochemically stable and further capable of being administered for treatment over a long period. As a result they have found cycloheptenopyridine derivates having a potent inhibitory action on gastric acid secretion and a cytoprotection together.

Thus, according to this invention are provided cycloheptenopyridine derivatives represented by the general formula

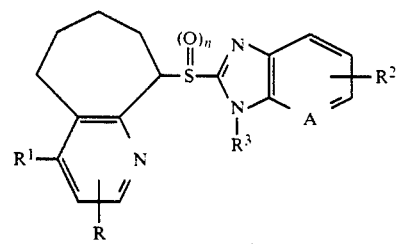

[wherein R represents a hydrogen atom or lower alkyl group; $R^1$ represents a hydrogen atom, halogen atom, lower cycloalkoxy group, amido group, substituted phenoxy group, substituted benzyloxy group, lower alkoxy group optionally containing halogen atom(s), nitro group, hydroxyl group, lower alkenyloxy group, lower alkylthio group, or a group —$NR^4R^5$ (wherein $R^4$ and $R^5$ may be the same or different and each represents a hydrogen atom or lower alkyl group, or $R^4$ and $R^5$ mutually combine together with the nitrogen atom adjacent thereto to form a 5- or 6- membered heterocyclic group; $R^2$ represents a hydrogen atom, halogen atom, lower alkyl group optionally containing a halogen atom, lower alkoxy group optionally containing a halogen atom, hydroxyl group, acyl group, lower alkoxycarbonyl group, nitro group or amino group; $R^3$ represents a hydrogen atom, a lower alkyl group, lower alkoxymethyl group, lower alkylcarbonyl group, lower alkoxycarbonyl group, carbamoyl group, lower alkylcarbamoyl group, lower alkylcarbonylmethyl group, lower alkoxycarbonylmethyl group, lower acyloxymethyl group, lower alkylsulfonyl group, or physiologically acceptable protective group eliminatable in an acid medium or under a physiological condition; n represents 0 or 1; and A represents a methine carbon or nitrogen atom] or their salts.

Cycloheptenopyridine derivatives represented by the general formula [I] include stereoisomers such as tautomers derived from the partial structure of benzimidazole, diastereomers derived from the partial structure of cycloheptenopyridine, enantiomers based on the asymmetric center, and the like.

Specific examples of R in the general formula [I] include, for example, a hydrogen atom, a lower alkyl group having 1 to 6 carbon atoms such as methyl, ethyl, propyl or butyl, etc.

Specific examples of $R^1$ in the general formula [I] include, for example, a hydrogen atom; a halogen atom such as a chlorine, bromine, iodine or fluorine atom; a lower alkoxy group having 1 to 6 carbon atoms such as methoxy, ethoxy, n-propoxy, isopropoxy, n-butoxy, sec-butoxy, tert-butoxy or n-pentoxy; a lower alkenyloxy group such as allyloxy or butenyloxy; a lower alkoxy group substituted by halogen atom(s) such as 2,2,2-trifluoroethoxy or 2,2,3,3,3-pentafluoropropoxy; a lower alkoxy group substituted by a methoxy, ethoxy or n-propoxy group or the like; a lower alkoxy group substituted by a cyclopropoxy, cyclopropylmethyloxy, cyclopentyloxy or cyclohexyloxy group or the like; a lower alkoxy group containing an aromatic ring such as phenyloxy, tolyloxy, pyridyloxy or benzyloxy; a hydroxyl group; an amino group; a mono- or di-lower ($C_1$ to $C_6$) alkylamino group such as methylamino, dimethylamino, ethylamino, diethylamino, isopropylamino, n-propylamino, n-butylamino or tert-butylamino; a cyclic amino group to form a 5- or 6 membered ring such as pyrrolidino, piperidino, morpholino, piperazino, N-methylpiperazino or the like; etc.

Specific examples of $R^2$ in the general formula [I] include, for example, a hydrogen atom; a halogen atom such as a chlorine, bromine, iodine or fluorine atom; a lower alkyl group having 1 to 6 carbon atoms such as methyl, ethyl, n-propyl, isopropyl, n-butyl, isobutyl, sec-butyl or tert-butyl; a lower alkoxy group having 1 to 6 carbon atoms such as methoxy, ethoxy, n-propoxy, isopropoxy, n-butoxy, sec-butoxy, tert-butoxy or n-pentoxy; a lower alkyl or lower alkoxy group substituted by halogen atom(s) such as trifluoromethyl, 2-fluoroethyl, difluoromethyl, 2,2,2-trifluoroethoxy or 2,2,3,3,3-pentafluoropropoxy; a hydroxyl group; an acyl group having 1 to 6 carbon atoms such as acetyl, propionyl or butyryl; an aroyl group such as benzoyl; a lower alkoxycarbonyl group having 1 to 6 carbon atoms such as methoxycarbonyl, ethoxycarbonyl, n-propoxycarbonyl, isopropoxycarbonyl, n-butoxycarbonyl, sec-butoxycarbonyl, tert-butoxycarbonyl or n-pentoxycarbonyl; a nitro group; an amino group (including a lower alkylamino group); etc.

Specific examples of $R^3$ in the general formula [I] include, for example, a hydrogen atom; a lower alkyl group having 1 to 6 carbon atoms such as methyl, ethyl, n-propyl, isopropyl, n-butyl, isobutyl, sec-butyl or tert-butyl; a lower alkoxymethyl group such as methoxymethyl, ethoxymethyl or propoxymethyl; an acyl group having 1 to 6 carbon atoms such as acetyl, propionyl or butyryl; an aroyl group such as benzoyl; an acyloxymethyl group having 1 to 6 carbon atoms such as acetoxymethyl, propionyloxymethyl or butyryloxymethyl; an aroyloxymethyl group such as benzoyloxymethyl or toluyloxymethyl; a lower alkoxycarbonyl group having 1 to 6 carbon atoms such as methoxycarbonyl, ethoxycarbonyl, n-propoxycarbonyl, isopropoxycarbonyl, n-butoxycarbonyl, sec-butoxycarbonyl, tert-butoxycarbonyl or n-pentoxycarbonyl; a carbamoyl group, or a carbamoyl group substituted by a lower alkyl group having 1 to 6 carbon atoms such as methyl, ethyl, n-propyl, isopropyl, n-butyl, isobutyl, sec-butyl or tert-butyl; a lower alkylsulfonyl group having 1 to 6 carbon atoms whose lower alkyl moiety is exemplified by methyl, ethyl, n-propyl, isopropyl, n-butyl, isobutyl, sec-butyl, tert-butyl or the like; etc.

As salts of the compounds of the invention are mentioned pharmacologically acceptable addition salts with suitable alkali metal ions. Mentioned for example are salts with sodium, potassium, calcium, magnesium, etc.

Compounds [I] are mainly characterized by having a cycloheptenopyridine ring, and formation and introduction of this cycloheptenopyridine ring as well as formation and introduction of the benzimidazole ring and imidazopyridine ring can be carried out according to any pertinent synthetic method.

(a) Formation of the Cycloheptenopyridine Ring

Some of 9-hydroxy-2,3-cycloheptenopyridine derivatives having a cycloheptenopyridine ring and represented by the formula [IIa]

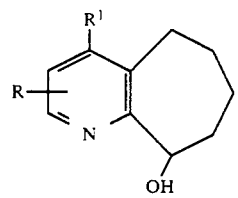

(wherein R and $R^1$ are as defined above) are novel substances, and can be synthesized by the synthetic route shown below.

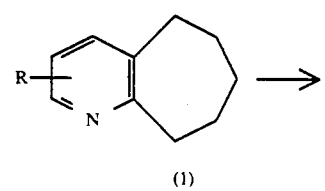

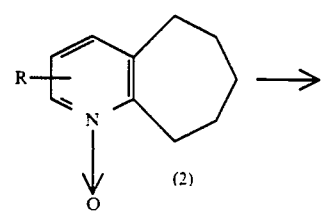

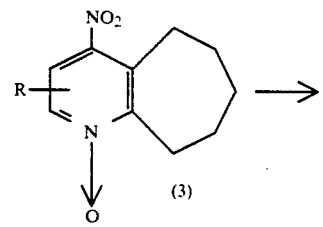

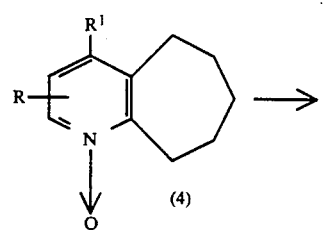

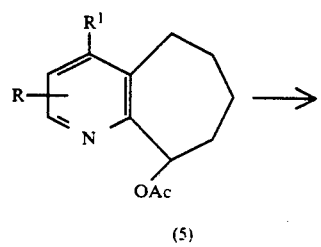

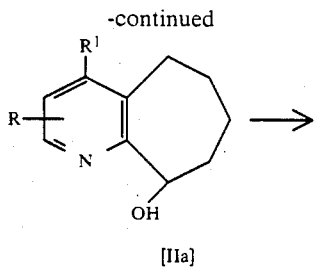

[IIa]

Namely a compound [IIa] can be synthesized by subjecting to a known oxidation reaction of a substituted or unsubstituted 2,3-cycloheptenopyridine derivative (1) either commercially available or synthesized according to a method disclosed in the literature [Yakugaku Zasshi (Journal of Pharmacology) 78 268 (1975); J. AM. CHEM. SOC., 79 402 (1957); J.C.S., Perkin Transl 1973 (9) 968.], nitrating the resulting 2,3-cycloheptenopyridine derivative (2), subjecting the resulting nitrated compound to substitution reaction(s) to form the corresponding 4-substituted-2,3-cycloheptenopyridine-N-oxide derivative (4), rearranging the compound (4) with heating in the presence of acetic anhydride, and hydrolyzing the resulting compound with an alkali.

Preparation of the compound (3) from the compound (2) can be carried out by direct nucleophilic substitution of the compound (2). Further, an alkoxy derivative or amine derivative can be obtained by first converting a compound (2) to the corresponding 4-halo-2,3-cycloheptenopyridine-N-oxide derivative and then reacting the 4-halo derivative, for example in the presence of a base, either with an alcohol such as methanol, ethanol, propanol, allyl alcohol, 2,2,2-trifluoroethanol, 2,2,3,3-tetrafluorpropanol, benzyl alcohol or methoxyethyl alcohol, or with ammonia or an amine such as methylamine, ethylamine, dimethylamine, piperazine, piperidine, pyrrolidine, morpholine or N-methylpiperazine.

This reaction can be carried out in the presence of a base at an appropriate temperature from ice-cooling to the boiling point of the solvent either using a nucleophilic reagent itself represented by $R^1$ as a solvent or using an organic solvent such as tetrahydrofuran, dioxane, acetone, acetonitrile, N,N-dimethylformamide or hexamethyl phosphoric triamide. When an amine derivative is obtained, the reaction is carried out, preferably in a sealed tube, for about 1 to 48 hours. Examples of bases used in this reaction include alkali metals such as sodium, potassium and lithium; alkali metal hydrides such as sodium hydride and potassium hydride; alcoholates such as potassium t-butylate and sodium methylate; alkali metal hydroxides such as lithium hydroxide, sodium hydroxide and potassium hydroxide; and alkali metal carbonates such as sodium hydrogen carbonate and potassium hydrogen carbonate. The resulting compound (4) is heated (80° to 150° C.) in the presence of acetic anhydride alone or sulfuric acid or perchloric acid or the like to give the corresponding 9-acetoxy-2,3-cycloheptenopyridine derivative (5), which is then hydrolyzed in the presence of a base, for example, an alkali metal hydroxide such as sodium hydroxide or potassium hydroxide, or an alkali metal carbonate such as sodium hydrogen carbonate or potassium hydrogen carbonate, whereby the corresponding compound [IIa] can be prepared. Examples of the solvent used include methanol, ethanol, water, etc. The reaction is usually completed in 10 minutes to 2 hours at a temperature of room temperature to the boiling point of the solvent.

(b) Synthesis of Compounds [I]

Compounds of the formula [I] can be synthesized according to various methods. For example, a reactive derivative represented by the general formula

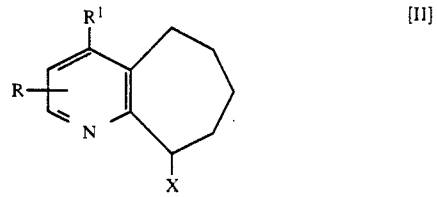

(wherein X represents a halogen atom, or an alkylsulfonyl or arylsulfonyl group, and R and $R^1$ are as defined above) is reacted with a 2-mercaptobenzimidazole or 2-mercapto[4,5-b]imidazopyridine derivative represented by the general formula

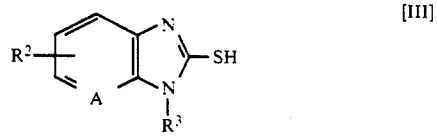

(wherein $R^2$, $R^3$ and A are as defined above) or a salt thereof to prepare a sulfide type compound [Ib] where n in the general formula [1] expresses zero.

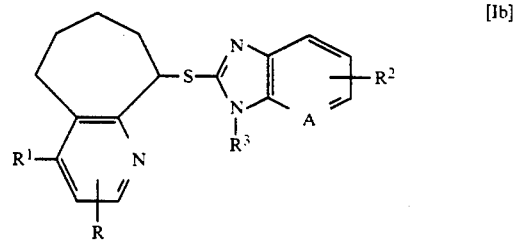

A reactive derivative [II] can be obtained either by reacting a compound [IIa] with a halide such as thionyl chloride, phosphorus oxychloride, phosphorus trichloride, phosphorus tribromide, p-toluenesulfonyl chloride or the like, or by reacting an aforementioned compound (4) with a halogenating reagent such as thionyl chloride, phosphorus oxychloride, phosphorus trichloride, p-toluenesulfonyl chloride or 1,3,5-trichlorocyanuric acid.

A sulfide type compound [Ib] can also be obtained by reacting a reactive derivative [II] with a 2-mercaptobenzimidazole derivative or 2-mercapto[4,5-b]imidzaopyridine derivative represented by the general formula

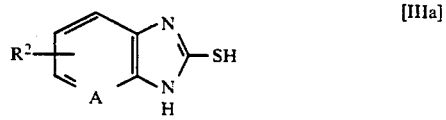

(wherein $R^2$ and A are as defined above) or a salt thereof to obtain a compound of the general formula

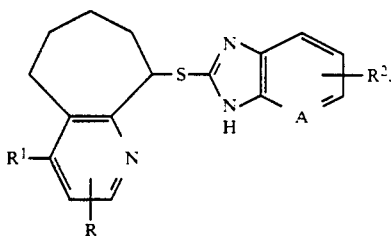

and then, if desired, subjecting the compound [Ia] to a known N-alkylation reaction, N-acylation reaction or N-sulfonylation reaction.

Specific examples of X in the reactive derivative [II] include, for example, halogen atoms such as chlorine, bromine and iodine atoms; lower alkylsulfonyloxy groups such as methanesulfonyloxy and ethanesulfonyloxy; arylsulfonyloxy groups such as benzenesulfonyloxy and p-toluenesulfonyloxy; etc. Examples of the salts of the compounds [III] and [IIIa] include salts with alkali metals such as sodium and potassium.

The reaction to condense a reactive derivative [II] with a compound [III] or [IIIa] is preferably carried out in a hydrophilic organic solvent such as methanol, ethanol, acetone, tetrahydrofuran, N,N-dimethylformamide or dimethylsulfoxide or in a mixed solvent of such a solvent and water. The reaction temperature is in the range of 0° to 150° C., preferably 80° to 100° C., and it is preferred that the reaction is carried out in the presence of a base.

Examples of the base include alkali metal hydroxides such as sodium hydroxide and potassium hydroxide; alkali metal carbonates such as sodium carbonate, potassium carbonate, sodium hydrogen carbonate and potassium hydrogen carbonate; organic amines such as triethylamine, pyridine and N,N-dimethylaniline; etc. The reaction is usually completed in 3 to 12 hours.

After completion of the reaction, the reaction solution is subjected to conventional methods, for example, the usually adopted means such as extraction, recrystallization and chromatography to obtain the compound [Ia] or [Ib].

Further, a sulfoxide type compound [Ic] which corresponds to a compound of the general formula [I] wherein n is 1 can be prepared by oxidizing a compound [Ia] or [Ib] or a salt thereof.

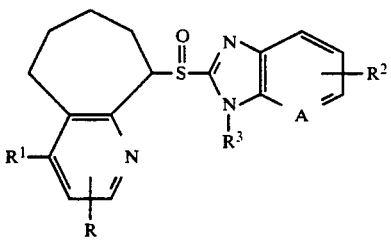

The oxidation reaction of a compound [Ia] or [Ib] can be carried out in benzene, chloroform, methylene chloride, methyl acetate, ethyl acetate, acetonitrile, methanol, N,N-dimethylformamide, N,N-dimethylacetamide, acetic acid, formic acid, water or another solvent or a mixed solvent thereof using an equivalent amount of an oxidizing agent. Usually, the reaction is carried out at −30° C. to room temperature and completed in 5 minutes to 2 hours. As examples of the oxidizing agent are mentioned oxidizing agents usually used for oxidation of sulfides such as peracetic acid, hydrogen peroxide, trifluoroperacetic acid, m-chloroperacetic acid and sodium metaperiodate. After completion of the reaction the compound [Ic] can be obtained from the reaction solution by conventional methods, for example, by usual separation and purification means such as extraction, recrystallization and chromatography.

The inhibitory action on gastric acid secretion and cytoprotection of the following compounds, which are representative examples of compounds [I] of the invention, are detailedly described below:

9-(5-Methoxybenzimidazole-2-yl)sulfinyl-4-methoxy-2,3-cycloheptenopyridine (compound of Example 63), 9-(Benzimidazole-2-yl)sulfinyl-4-methoxy-2,3-cycloheptenopyridine sodium salt (compound of Example 68), 9-(5-Methylbenzimidazole-2-yl)sulfinyl-2,3-cycloheptenopyridine (compound of Example 75), 9-(Benzimidazole-2-yl)sulfinyl-4-methoxy-2,3-cycloheptenopyridine (compound of Example 77), 9-(5-Fluorobenzimidazole-2-yl)sulfinyl-4-methoxy-2,3-cycloheptenopyridine (compound of Example 78), 9-(Benzimidazole-2-yl)sulfinyl-4-(2-methoxyethoxy)-2,3-cycloheptenopyridine (compound of Example 96), and 9-(Benzimidazole-2-yl)sulfinyl-4-methoxy-3-methyl-2,3-cycloheptenopyridine (compound of Example 109)

(a) Inhibitory Effect on Gastric Acid Secretion in Ghosh-Schild Rats

Each of male Wistar-KV rats was fasted for 24 hours, and a trachea cannula was set up under urethane anesthesia. The abdomen was incised, a double cannula was set up at the forestomach, and then the abdomen was closed. The gastric acid secretion was stimulated by intravenous infusion of 10 μg/kg/hr. Physiological saline was perfused into the stomach through the double cannula at a rate of 1 ml/min., and the effluent was collected every 10 minutes. The acidity of the effluent was measured, using an automatic titrator, by titrating the effluent with 1/100N sodium hydroxide to pH 7. When the acid secretion had reached a stable plateau, the test drug was intravenously administered, and the gastric acid secretion was measured 3 hours after the test drug administration. The antisecretory effect was expressed as percentages of the secretory amount before administration of the test compound. The results are shown in Table-1.

(b) Inhibitory Effect on Formation of Gastric Lesion Induced by Ethanol

Male Wistar rats weighing 170 to 270 g were used. Each of the rats was placed in separate cages to deprive of food but allowed free access to water for 4 hours. Test drugs or the control drug were orally administered respectively in amounts of 3, 10 and 30 mg/kg, and 30 minutes thereafter 1 ml of 99.5% ethanol were orally administered respectively. One hour after the ethanol administration the rats were sacrificed by cervical vertebrae dislocation, and the stomachs were removed with 8 ml of 1% formalin and put into 1% formalin for 30 minutes to fix the gastric wall. After the fixing, each stomach was opened along the greater curvature, and then after the mucosal surface was washed with tap water, the total length lesions generated at the glandub portion was determined as an ulcer index.

The antiulcer effect by the test drug was expressed by the ED50 value (the dose of the test compound to inhibit the ulcer by 50% to the ulcer index of the non-treated group). The results are shown in Table-2. Only the solvent was administered to the non-treated group.

TABLE 1

| Example No. | Inhibiting action of gastric acid secretion (rat i.v.) | |
|---|---|---|
| | 3 mg/kg | 1 mg/kg |
| 63 | 73.8% | 45.7% |
| 68 | — | 54.9% |
| 75 | 42.1% | — |
| 77 | 74.7% | 44.7% |
| 78 | 82.9% | 65.4% |
| 96 | 57.4% | 38.6% |
| 109 | 77.6% | — |
| Omeprazole (Control drug) | — | 36.9% |

Inhibition percentages at 180 minutes after the administrations are shown.

TABLE 2

| Example No. | ED$_{50}$ value (mg/kg P.O) |
|---|---|
| 77 | 13.0 |
| 68 | 10.9 |

As apparent from the above test results, compounds [I] are potent treatment drugs for gastric or duodenal ulcer.

An antiulcer agent containing as an active ingredient a compound of the formula [I] or a salt thereof can mainly be orally or parenterally administered (for example, administered by intramuscular injection, intravenous injection, subcutaneous administration, rectal administration, transcutaneous administration, or the like), and preferably can be orally administered. Various and various drug forms suitable for the respective administrations can be adopted. As for solid formulations, a compound [I] can be formulated into tablets, capsules, granules, powders or fine granules, and can also be formulated in enteric coated agents by a coating technique therefor. Further, a liquid agent can be prepared by converting a compound [I] to an alkali salt or physiologically acceptable salt, and then dissolving the salt in water or an aqueous alkali solution.

Although the dose of a compound [I] to patients is varied depending on the age, the condition of the disease and the like, it is generally preferred to administer it to an adult in an amount of 0.5 to 1,000 mg, particularly 1 to 200 mg, divided into 1 to 3 times, per day.

Syntheses of starting compounds used in the invention and compounds [I] of the invention are more specifically and detailedly described below according to reference examples and examples, but the invention should not be limited thereto.

REFERENCE EXAMPLE 1

2,3-Cycloheptenopyridine-N-oxide 1) 14.72 g (0.1 mol) of 2,3-Cycloheptenopyridine is dissolved in 150 ml of dichloromethane, 21.57 g (0.1 mol) of m-chloroperbezoic acid is added by portions under ice cooling and stirring, and the mixture is stirred at the same temperature for 3 hours. After the reaction, 150 ml of a saturated aqueous sodium hydrogen carbonate solution is added, followed by extraction with methylene chloride. The methylene chloride layer is sufficiently washed with a saturated aqueous sodium hydrogen carbonate solution and saturated saline, and dried over anhydrous magnesium sulfate, and the solvent is distilled away under reduced pressure. The resulting solid residue is recrystallized from ether-n-hexane to obtain 14.13 g (86.6 %) of 2,3-cycloheptenopyridine-N-oxide as grayish white crystals having a melting point of 107° to 109° C.

IR$\nu$ max(KBr): 3080, 2924, 1610, 1432, 1268, 1246, 810 cm$^{-1}$.

NMR(CDCl$_3$)$\delta$: 1.09–2.03(6H,m), 2.57–2.91 (2H,m), 3.18–3.50(2H,m), 6.68–7.03(2H,m), 7.92–8.23(1H,m).

2) 14.72 g (0.1 mol) of 2,3-cycloheptenopyridine is dissolved in 100 ml of acetic acid, and 13.3 ml of 30 % aqueous hydrogen oxide is added, followed by 8 hour stirring with heating at 100° C. 7.4 ml of 30% Aqueous hydrogen oxide is further added, and then after 8 hour stirring with heating, the solvent is distilled away under reduced pressure. The resulting residue is extracted with chloroform, and the extract is sufficiently washed with a saturated aqueous sodium hydrogen carbonate solution and saturated saline and dried over anhydrous magnesium sulfate. Then, the solvent is distilled away under reduced pressure to obtain almost quantitatively 2,3-cycloheptenopyridine-N-oxide.

REFERENCE EXAMPLE 2

4-Nitro-2,3-cycloheptenopyridine-N-oxide 3.92 g (24 mmoles) of 2,3-cycloheptenopyridine-N-oxide is dissolved in 15 ml of sulfuric acid under ice cooling, and the solution is stirred for 40 minutes with heating at 85° to 90° C., while 13 ml of fuming nitric acid is added dropwise thereto. After the reaction, ice water is added, and after neutralization with a 40% aqueous sodium hydroxide solution, the mixture is extracted with methylene chloride. The methylene chloride layer is washed with saturated saline and dried over anhydrous magnesium sulfate, and the solvent is distilled away under reduced pressure to obtain 2.23 g (44.6%) of 4-nitro-2,3-cycloheptenopyridine-N-oxide as yellowish crystals having a melting point of 118° to 120° C.

IR$\nu$ max(KBr): 3110, 2928, 2852, 1529, 1570, 1516, 1422, 1340, 1272, 1144, 828, 700 cm$^{-1}$.

NMR(CDCl$_3$)$\delta$: 1.54–2.08(6H,m), 2.85–3.17 (2H,m), 3.27–3.63(2H,m), 7.46 (1H,d,J=8 Hz), 8.11(1H,d,J=8 Hz).

REFERENCE EXAMPLE 3

4-chloro-2,3-cycloheptenopyridine-N-oxide 2.23 g (10.7 mmol) of 4-Nitro-2,3-cycloheptenopyridine-N-oxide is added by portions to 7.85 g (0.1 mol) of acetyl chloride under ice cooling and stirring, and the mixture is stirred at the same temperature for 1 hour. After the reaction, the mixture is poured into ice water, followed by extraction with ethyl acetate. The ethyl acetate layer is washed with saturated saline and dried over anhydrous magnesium sulfate, and the solvent is distilled away under reduced pressure. The resulting residue is purified by silica gel column chromatography (chloroform-methanol 95:5) and recrystallized from ether-n-hexane to obtain 1.77 g (83.9%) of 4-chloro-2,3-cycloheptenopyridine-N-oxide as yellowish prismatic crystals having a melting point of 117° to 118° C.

IRν max(KBr): 3112, 2924, 2848, 1438, 1418, 1336, 1256, 1170, 1110, 830, 710 cm$^{-1}$.

NMR(CDCl$_3$)δ: 1.50–2.05(6H,m), 2.80–3.15 (2H,m), 3.22–3.55(2H,m), 7.03 (1H,d,J=8 Hz), 7.99(2H,d,J=8 Hz).

REFERENCE EXAMPLE 4

4-Methoxy-2,3-cycloheptenopyridine-N-oxide 810 mg (3.89 mmol) of 4-mitro-2,3-cycloheptenopyridine-N-oxide is dissolved in 10 ml of methanol, 250 mg of sodium hydroxide is added thereto, and the mixture is refluxed for 45 minutes. After cooling the methanol is distilled away under reduced pressure, the resulting residue is extracted with chloroform. The chloroform layer is washed with saturated saline and dried over anhydrous magnesium sulfate, and the solvent is distilled away under reduced pressure. The resulting residue is purified by silica gel column chromatography (chloroform-methanol 95:5) and recrystallized from ethyl acetate to obtain 710 mg (94.5%) of 4-methoxy-2,3-cycloheptenopyridine-N-oxide as yellowish prismatic crystals having a melting point of 148° to 149° C.

IRν max (KBr): 3075, 2916, 2848, 1615, 1570, 1460, 1428, 1344, 1284, 1242, 1188, 1034, 828, 746 cm$^{-1}$.

NMR(CDCl$_3$)δ: 1.43–2.04(6H,m), 2.65–2.97(2H,m), 3.20–3.54(2H,m), 3.83(3H,s), 6.57(1H,d,J=8 Hz), 8.08(1H,d,J=8 Hz).

REFERENCE EXAMPLE 5

4-(3-Methoxypropoxy)-2,3-cycloheptenopyridine-N-oxide 1.28 g (14.2 mmol) of 1-methoxypropanol is dissolved in 7 ml of dimethylsulfoxide (DMSO) in an argon stream, 566 mg (14.2 mmol) of 60% sodium hydride is added thereto, and the mixture is stirred at 60° C. for 30 minutes. Under stirring at room temperature, 1.40 g (7.08 mmol) of 4-chloro-2,3-cycloheptenopyridine-N-oxide dissolved in 5 ml of DMSO is added dropwise, followed by stirring at 40° C. for 1 hour. Thereafter, with stirring at room temperature, 566 mg (14.2 mmol) of 60% sodium hydride and 310 mg (3.44 mmol) of 1-methoxypropanol are addded, and the mixture is stirred at 40° C. for 16 hours. After cooling the reaction mixture is poured in ice-saline, followed by extraction with chloroform. The chloroform layer is washed with saturated saline and dried over anhydrous magnesium sulfate, and the solvent is distilled away under reduced pressure. The resulting residue is purified by silica gel column chromatography (chloroform-methanol 40:1) to obtain 1.15 g (64.5%) of 4-(3-methoxypropoxy)-2,3-cycloheptenopyridine-N-oxide as a pale brown oily substance.

IRν max(Neat): 2948, 2856, 1450, 1342, 1288, 1240, 1200, 1188, 1136, 1120, 1092, 1064, 1028, 750, 662 cm$^{-1}$.

NMR(CDCl$_3$)δ: 1.40–2.00(6H,m) 2.04(2H,t, J=6 Hz), 2.63–2.94(2H,m), 3.31 (3H,s), 3.20–3.65(4H,m), 4.04 (2H,t,J=7 Hz), 6.57(1H,d,j=7 Hz), 8.03(1H,d,J=7 Hz).

REFERENCE EXAMPLE 6

4-(2-benzyloxyethoxy)-2,3-cycloheptenopyridine-N-oxide

In a stream of argon, 804 mg (20.1 mmol) of 60% sodium hydride is suspended in 7 ml of DMSO, 2.86 ml (20.1 mmol) of 2-benzyloxyethanol is added dropwise with stirring at room temperature, and the mixture is stirred at 60° C. for 35 minutes. Further, 1.40 g (7.05 mmol) of 4-chloro-2,3-cycloheptenopyridine-N-oxide dissolved in 5 ml of DMSO is added dropwise thereto with stirring at room temperature, and the mixture is stirred at 40° C. for 3 hours and 20 minutes. After cooling, the reaction mixture is poured in ice water, followed by extraction with methylene chloride. The methylene chloride layer is washed successively with water and saturated saline and dried over anhydrous magnesium sulfate, and the solvent is distilled away under reduced pressure. The resulting residue is purified by silica gel column chromatography (chloroform-methanol 40:1) to obtain 2.12 g (96.1%) of 4-(2-benzyloxyethoxy)-2,3-cycloheptenopyridine-N-oxide as a pale brown oily substance.

IRν max(Neat): 2924 2852, 1444, 1342, 1290, 1242, 1200, 1166, 1134, 1092, 1068, 1034, 892, 758, 744, 690 cm$^{-1}$.

NMR(CDCl$_3$)δ: 1.43–2.05(6H,m), 2.70–3.00 (2H,m), 3.25–3.55(2H,m), 3.70–3.96(2H,m), 4.00–4.24(2H,m), 4.60(2H,s), 6.58(1H,d,J=8 Hz), 7.30(5H,bs), 8.04(1H,d,J=8 Hz).

REFERENCE EXAMPLE 7

4-(2-Hydroxyethoxy)-2,3-cycloheptenopyridine-N-oxide

In a stream of argon, 1.63 g (70.0 milligram atoms) of metal sodium is added by portions to 28 ml of ethylene glycol under ice cooling and stirring, and the mixture is stirred for 1 hour with heating at 100° C. Then, 7.00 g (35.0 mmol) of 4-chloro-2,3-cycloheptenopyridine-N-oxide is added with stirring at room temperature, and the mixture is stirred at 120° C. for 3 hours and 30 minutes. After the reaction, the mixture is poured in ice water, followed by extraction with chloroform. The chloroform layer is dried over anhydrous magnesium sulfate, and the solvent is distilled away under reduced pressure. The resulting residue is crystallized from ethanol-ether to give 3.09 g (38.9%) of 4-(2-hydroxyethoxy)-2,3-cycloheptenopyridine-N-oxide as colorless pillar crystals having a melting point of 159°–160° C. The mother liquor is concentrated, and the residue is purified by silica gel column chromatography (chloroform-methanol 20:1→15:1→10:1) to give 2.62 g (33.4% of the desired substance (total yield 72.3%).

IRν max(KBr): 3224, 3104, 2912, 2852, 1450, 1344, 1292, 1236, 1204, 1186, 1138, 1092, 1062, 1032, 890, 822, 758 cm$^{-1}$.

NMR(CDCl$_3$)δ: 1.35–2.10(6H,m), 2.65–3.03(2H,m), 3.22–3.55(2H,m), 3.55–4.15(5H,m), 6.57(1H,d,J=7 Hz), 7.97(1H,d,J=7 Hz).

REFERENCE EXAMPLE 8

4-(2-Chloroethoxy)-2,3-cycloheptenopyridine-N-oxide

In a stream of argon, 2.23 g (10.0 mmol) of 4-(2-hydroxyethoxy)-2,3-cycloheptenopyridine-N-oxide is dissolved in 22 ml of chloroform, 1.97 ml (27.0 mmol) of thionyl chloride is added dropwise thereto with stirring at −12° C., and the mixture is stirred at room temperature for hours and 20 minutes and then stirred at 60° C. for 1 hour and 15 minutes. After cooling, the reaction mixture is poured into ice—a saturated aqueous sodium hydrogen carbonate solution, followed by extraction with chloroform. The chloroform layer is washed successively with a saturated aqueous sodium hydrogen carbonate solution and water and dried over anhydrous magnesium sulfate, and then the solvent is distilled away under reduced pressure. The resulting residue is purified by silica gel column chromatography (chloroform-methanol 20:1) to give 2.15 g (89.1%) of 4-(2-chloroethoxy)-2,3-cycloheptenopyridine-N-oxide as colorless needle crystals having a melting point of 109° to 110.5° C.

IRν max(KBr): 2924 2852, 1448, 1292, 1240, 1200, 1190, 1068, 1032, 824, 814, 774 cm$^{-1}$.

NMR(CDCl$_3$)δ: 1.39-2.01(6H,m), 2.66-3.00 (2H,m), 3.20-3.53(2H,m), 3.80 (2H,t,J=6 Hz), 6.55(1H,d,J=8 Hz), 8.05(1H,d,J=8 Hz).

REFERENCE EXAMPLE 9

4-[2-(2-pyridylmethoxy)ethoxy]-2,3-cycloheptenopyridine-N-oxide

In a stream of ar9on, 2.23 9 (10.0 mmol) of 4-(2-hydroxyethoxy)-2,3-cycloheptenopyridine-N-oxide is suspended in 30 ml of tetrahydrofuran (THF), 600 mg (15.0 mmol) of 60% sodium hydride is added by portions thereto under ice cooling and stirring, and the mixture is stirred at room temperature for 10 minutes. Then, after 20 minutes stirring at 50° C., 1.65 g (12.90 mmol) of picolyl chloride dissolved in 15 ml of THF is added dropwise thereto with stirring at room temperature, and the mixture is stirred at 90° C. for 8 hours. Then, after 12 hours stirring at room temperature, 200 mg (5 mmol) of 60% sodium hydride is added, and the mixture is refluxed with heating for 3 hours. After the reaction, the solvent is distilled away under reduced pressure, the risidue is addd to ice water, and the mixture is extracted with methylene chloride. The methylene chloride layer is dried over anhydrous magnesium sulfate, and the solvent distilled away under reduced pressure. The resulting residue is purified by silica gel column chromatography (chloroform-methanol 30:1→10:1) to give 2.33 g (74.2%) of 4-[2-(2-pyridylmethoxy)ethoxy]-2,3-cycloheptenopyridine-N-oxide as a brown oily substance.

IRν max(Neat): 2924 2852, 1590, 1446, 1342, 1290, 1240, 1200, 1134, 1092, 1064, 1036, 892, 758 cm$^{-1}$.

NMR(CDCl$_3$)δ: 1.37-2.02(6H,m), 2.70-3.02 (2H,m), 3.21-3.51(2H,m), 3.80-4.03(2H,m), 4.05-4.31(2H,m), 6.59(1H,d,J=8 Hz), 7.03-7.78 (3H,m), 8.04(1H,d,J=8 Hz), 8.51 (1H,d,J=8 Hz).

REFERENCE EXAMPLE 10

4-[2-(2-oxopyrrolidin-1-yl)ethoxy]-2,3-cycloheptenopyridine-N-oxide

In a stream of argon, 632 mg (15.8 mmol) of 60% sodium hydride is suspended in 30 ml of dimethylformamide (DMF), 1.12 g (13.1 mmol) of 2-pyrrolidone is added thereto under ice cooling. and the mixture is stirred at 80° C. for 1 hour and 30 minutes. Then, under stirring at room temperature, 2.11 g (8.73 mmol) of 4-(2-chloroethoxy)-2,3-cycloheptenopyridine-N-oxide dissolved in 15 ml of DMF is added dropwise, and the mixture is stirred at 60° C. for 2 hours and 10 minutes. After cooling, the mixture is poured into a saturated aqueous sodium hydrogen carbonate solution, followed by extraction with methylene chloride. The methylene chloride layer is dried over anhydrous magnesium sulfate, and the solvent is distilled away under reduced pressure. The resulting residue is subjected to separation and purification by silica gel column chromatography (chloroform-methanol 20:1→10:1→4:1) to obtain 334 mg (53.3%) of 4-[2-(2-oxypyrrolidin-1-yl)ethoxy]-2,3-cycloheptenopyridine-N-oxide as colorless powder having a melting point of 112° to 115° C.

IRν max(KBr): 2924, 1672, 1452, 1344, 1292, 1240, 1202, 1188, 1138, 1092, 1068, 1028, 886, 832, 758 cm$^1$.

NMR(CDCl$_3$)δ: 1.40-2.56(10H,m), 2.65-3.00 (2H,m), 3.25-3.62(4H,m), 3.68 (2H,t,J=6 Hz), 4.09(2H,t,J=6 Hz), 6.55(1H,d,J=8 Hz), 8.04(1H,d,J =8 Hz)

REFERENCE EXAMPLE 11

4-Ethoxy-3-methyl-2,3-cycloheptenopyridine-N-oxide 1.00 g (4.50 mmol) of 4-nitro-3-methyl-2,3-cycloheptenopyridine-N-oxide is dissolved in 15 ml of ethanol, 540 mg (13.5 mmol) of sodium hydroxide is added thereto under ice cooling and stirring, and after stirring at room temperature for 19 hours, the mixture is refluxed with heating for 30 minutes. Ater cooling, the ethanol is distilled away under reduced pressure and the resulting residue is extracted with chloroform. The chloroform layer is washed successively with water and saturated saline and dried over anhydrous magnesium sulfate, and the solvent is distilled away under reduced pressure. The resulting residue is purified by silica gel column chromatography (chloroform-methanol 40:1) to obtain 679 mg (68.2%) of 4-ethoxy-3-methyl-2,3-cycloheptenopyridine-N-oxide as pale brown powder having a melting point of 107° to 108° C.

IRν max(KBr): 2976, 2932, 2852, 1478, 1454, 1420, 1388, 1332, 1248, 1228, 1192, 1168, 1136, 1052, 1026, 966, 928, 868 cm$^{-1}$.

NMR(CDCl$_3$)δ: 1.42(3H,t,J=7 Hz), 1.50-2.03 (6H,m), 2.16(3H,s), 2.65-3.93 (2H,m), 3.23-3.48(2H,m), 3.81 (2H,q,J=7 Hz), 7.95(1H,s).

Compounds shown in Table-3 are obtained in the same manner as Reference examples 1 to 11.

TABLE 3

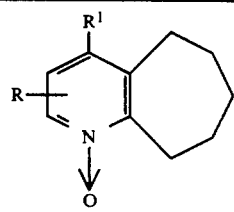

| Reference Example No. | R | R$^1$ | Melting point (yield) | IRνcm$^{-1}$ | NMR(CDCl$_3$)δ |
|---|---|---|---|---|---|
| 12 | H | OCH$_2$CH$_2$OCH$_3$ | Palely brown pillar crystal (56.0%) 71-73° C. | (KBr) 3016, 2980, 2920, 2872, 2852, 1454, 1292, 1240, 1202, 1190, 1136, 1120, 1092, 1064, 1034, 760. | 1.41-2.00(6H, m), 2.66-3.03(2H, b, J=10Hz), 3.41(5H, bs), 3.58-3.86 (2H, m), 3.96-4.30(2H, m), 6.57(1H, d, J=8Hz), 8.03(1H, d, J=8Hz) |
| 13 | H | OCH$_2$CH$_2$=CH$_2$ | Colorless | (KBr) 2916, 1448, 1422, 1344, | 1.40-2.03(6H, m), 2.70-3.30(2H, m), |

TABLE 3-continued

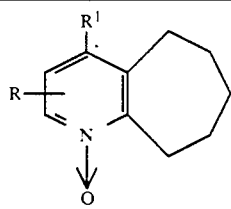

| Reference Example No. | R | R¹ | Melting point (yield) | IR νcm⁻¹ | NMR(CDCl₃)δ |
|---|---|---|---|---|---|
|  |  |  | amorphous powder (50.9%) 149–150° C. | 1292, 1238, 1204, 1188, 1138, 1062, 1028, 1000, 924, 884, 826, 810, 766, 744. | 3.20–3.55(2H, m), 4.52(2H, d, J=5Hz), 5.10–5.58(2H, m), 5.76–6.23 (1H, m), 6.56(1H, d, J=7Hz), 8.03 (1H, d, J=7Hz) |
| 14 | H | OCH₂CF₃ | Colorless needle crystal (48.6%) 166–169° C. | (KBr) 2920, 2944, 1454, 1296, 1274, 1240, 1202, 1174, 1160, 1134, 1098, 1038, 972, 862, 764. | 1.40–2.17(6H, m), 2.60–3.04(2H, m), 3.16–3.56(2H, m), 4.35(2H, q, J=8Hz, 16Hz), 6.55(1H, d, J=8Hz), 8.07 (1H, d, J=8Hz) |
| 15 | H | OCH₂CF₂CF₃ | Colorless prismatic crystal (72.8%) 135–138° C. | (KBr) 2940, 1454, 1346, 1298, 1272, 1240, 1216, 1188, 1110, 1094, 1068, 1040, 1026, 956, 810, 764. | 1.45–2.05(6H, m), 2.70–2.97(2H, m), 3.25–3.50(2H, m), 4.40(2H, t, J=12Hz), 6.55(1H, d, J=5Hz), 8.08 (1H, d, J=5Hz) |
| 16 | H | OCH₂CF₂CHF₂ | Colorless powder (60.0%) 106.5–108° C. | (KBr) 2936, 1478, 1452, 1346, 1296, 1270, 1240, 1200, 1136, 1098, 1068, 1036, 962, 950, 886, 840, 832, 810, 768. | 1.45–2.05(6H, m), 2.68–2.95(2H, m), 3.25–3.50(2H, m), 4.35(2H, t, J=12Hz), 5.36, 5.96, 6.52(1H, t×3, J=3Hz), 6.57(1H, d, J=6Hz), 8.07 (1H, d, J=6Hz) |
| 17 | H | O(CH₂)₂OPh | Palely brown powder (70.5%) 149.5–152° c. | (KBr) 2924, 1490, 1452, 1438, 1282, 1236, 1198, 1180, 1134, 1086, 1068, 930, 896, 832, 760. | 1.38–2.03(6H, m), 2.66–2.93(2H, m), 3.25–3.55(2H, m), 4.29(4H, s), 6.62(1H, d, J=7Hz), 6.74–7.40 (5H, m), 8.05(1H, d, J=7Hz) |
| 18 | H | (morpholino-O-CH₂) | Colorless powder (62.0%) 152–153° C. | (KBr) 2956, 2916, 2852, 1446, 1346, 1264, 1246, 1190, 1136, 1112, 1064, 1006, 988, 932, 890, 874, 856, 732. | 1.50–2.49(6H, m), 2.70–3.23(6H, m), 3.23–3.65(2H, m), 3.72–4.00(4H, m), 6.67(1H, d, J=6Hz), 8.05(1H, d, J=6Hz) |
| 19 | H | SCH₂CH₂CH₃ | Colorless amorphous powder (79.6%) — | (KBr) 3432, 3068, 2960, 2924, 2848, 2824, 1426, 1336, 1268, 1242, 1214, 1194, 1130, 1090, 1038, 1000, 880, 828, 742, 700, 634, 556. | 106(3H, t, J=6Hz), 1.46–2.03 (8H, m), 2.52–3.15(4H, m)3.20–3.52 (2H, m), 6.87(1H, d, J=6Hz), 8.02 (1H, d, J=6Hz) |
| 20 | 3-CH₃ | 4-OCH₂CF₂CF₂H | Palely brown oily substance (100%) — | (neat) 2932, 1455, 1419, 1296, 1272, 1248, 1224, 1197, 1170, 1110, 1068, 1050, 1032, 753. | 1.50–2.01(6H, m), 2.19(2H, s), 2.69–2.95(2H, m), 3.20–3.50(2H, m), 4.11(2H, t, J=12Hz), 5.46, 6.05, 6.63(1H, t×3, J=4Hz), 7.98(1H, s) |
| 21 | H | OEt | Palely brown powder (74.3%) 148–149.5° C. | (KBr) 3320, 2924, 1448, 1290, 1236, 1190, 1138, 1116, 1066, 1038, 894. | 1.30–1.96(6H, m), 1.43(3H, t, J=7.5Hz), 2.69–2.96(2H, m), 3.26–3.53(2H, m), 4.02(2H, q, J=7.5Hz), 6.53(1H, d, J=9Hz), 8.04(1H, d, J=9Hz) |
| 22 | H | O-n-Bu | Paleley brown amorphous powder (54.8%) | (KBr) 3384, 2952, 2920, 2852, 1450, 1406, 1290, 1240, 1198, 1188. | 0.96(3H, t, J=7.5Hz), 1.16–2.35 (10H, m), 2.73–3.05(2H, m), 3.18–3.56(2H, m), 3.94(2H, t, J=7.5Hz), 6.53(1H, d, J=9Hz), 8.03(1H, d, J=9Hz) |
| 23 | H | O-C₆H₄-CH₃ (para) | Palely brown oily substance (72.5%) — | (neat) 3032, 2924, 1604, 1506, 1442, 1270, 1246, 1198, 1166, | 1.33–2.20(6H, m), 2.32(3H, s), 2.73–3.06(2H, m), 3.28–3.56(2H, m), 6.43(1H, d, J=9Hz), 6.81(2H, d, J=10.5Hz), 7.15(2H, d, J=10.5Hz), 7.96(1H, d, J=9Hz) |
| 24 | H | OCH₂-cyclopropyl | Palely brown amorphous powder (92.6%) | (KBr) 3068, 2976, 2924, 1612, 1450, 1412, 1342, 1292, 1138, 1062, 1028. | 0.19–0.81(4H, m), 1.03–1.36(1H, m), 1.40–2.06(6H, m), 2.71–3.03(2H, m), 3.24–3.58(2H, m), 3.80(2H, d, J=7.5Hz), 6.57(1H, d, J=9Hz), 8.04(1H, d, J=9Hz) |
| 25 | H | OCH₂-tetrahydrofuryl | Palely brown oily substance (75.3%) | (neat) 3376, 2976, 2928, 2856, 1614, 1446, 1292, 1238, 1186, 1136, 1082, 1066. | 1.35–2.23(10H, m), 2.54–2.96 (2H, m), 3.23–3.57(2H, m), 3.65–4.06(4H, m), 4.06–4.43(1H, m), 6.58(1H, d, J=9Hz), 8.04(1H, d, J=9Hz) |
| 26 | 3-CH₃ | H | Colorless powder | (neat) 3400, 2911, 2842, 1448, 1340, 1289, 1203, 1141, 1043, | 1.50–1.97(6H, m), 2.20(3H, s), 2.62–2.87(2H, d, J=11Hz), |

TABLE 3-continued

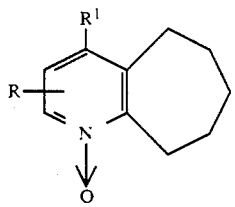

| Reference Example No. | R | R¹ | Melting point (yield) | IR $\nu$ cm$^{-1}$ | NMR(CDCl$_3$)$\delta$ |
|---|---|---|---|---|---|
| 27 | 3-CH$_3$ | OCH$_3$ | (88.7%) — Palely brown powder (100%) 108–109° C. | (KBr) 2932, 2848, 1479, 1460, 1404, 1344, 1296, 1250, 1198, 1006. | 3.21–3.48(2H, d, J=11Hz), 6.80(1H, s), 7.97(1H, s) 1.42–2.06(6H, m), 2.16(3H, s), 2.65–2.95(2H, m), 3.20–3.46(2H, m), 3.68(3H, s), 7.95(1H, s) |
| 28 | 3-CH$_3$ | SCH$_2$CH$_2$CH$_3$ | Colorless amorphous powder (96.8%) — | (KBr) 2962, 2920, 2848, 1464, 1446, 1290, 1230, 1140, 651. | 0.86–1.12(3H, t, J=7Hz), 1.30–2.02(8H, m), 1.40(3H, s), 1.48–1.73(2H, t, J=7Hz), 3.15–3.47(4H, m), 8.00(1H, s) |

REFERENCE EXAMPLE 29

9-Acetoxy-2,3-cycloheptenopyridine 20 ml of acetic anhydride is added 4.9 g (30 mmol) of 2,3-cycloheptenopyridine-N-oxide, and the mixture is refluxed at 90° C. for 15 hours. After cooling, excessive acetic anhydride is distilled away under reduced pressure, and the resulting residue is extracted with ethyl acetate. The ethyl acetate layer is washed successively with a saturated aqueous sodium hydrogen carbonate solution and saturated saline and dried over anhydrous magnesium sulfate, and the solvent is distilled away under reduced pressure. The resulting residue is purified by silica gel column chromatography (ethyl acetate-n-hexane 1:3) to obtain 5.2 g (84.5%) of 9-acetoxy-2,3-cycloheptenopyridine as a yellowish oily substance.

IR$\nu$ max(neat): 3050, 2932, 2856, 1736, 1454, 1438, 1368, 1234, 1040 cm$^{-1}$.

NMR(CDCl$_3$)$\delta$: 1.50–2.30(6H,m), 2.16(3H,m), 2.63–3.13(2H,m), 5.80–6.05 (1H,m), 6.90–7.47(2H,m), 8.31 (1H,d,J=5 Hz).

The compounds of the following Reference examples 30 to 32 are obtained in the same manner as above.

REFERENCE EXAMPLE 30

9-Acetoxy-4-methoxy-2,3-cycloheptenopyridine

Yellowish oily substance
Yield: 76.5%

IR$\nu$ max(neat): 2932, 2856, 1736, 1580, 1476, 1372, 1288, 1236, 1046, 966 818, 754 cm$^{-1}$.

NMR(CDCl$_3$)$\delta$: 1.07–2.40(6H,m), 2.18(3H,m), 2.42–3.38(2H,m), 3.83(3H,s), 5.92(1H,bs), 6.67(1H,d,J=6 Hz), 8.24(1H,d,J=6 Hz).

REFERENCE EXAMPLE 31

9-Acetoxy-4-chloro-2,3-cycloheptenopyridine

Colorless oily substance
Yield: 53.2%

IR$\nu$ max(neat): 3045, 2936, 1742, 1558, 1452, 1370, 1234, 1054, 1026, 813 cm$^{-1}$.

NMR(CDCl$_3$)$\delta$: 1.20–2.35(6H,m), 2.23(3H,s), 2.58–3.63(2H,m), 5.88–6.14 (1H,m), 7.26(1H,d,J=5 Hz), 8.24 (1H,d,J=5 Hz).

REFERENCE EXAMPLE 32

9-Acetoxy-4-nitro-2,3-cycloheptenopyridine

Yellowish oily substance
Yield: 7.06%

IR$\nu$ max(neat): 3080, 2936, 2864, 1738, 1536, 1370, 1232, 1056, 842 cm$^{-1}$.

NMR(CDCl$_3$)$\delta$: 1.38–2.26(6H,m), 2.18(3H,s), 2.40–3.32(2H,m), 5.84–6.13 (1H,m), 7.30(1H,d,J=5 Hz), 8.48(1H,d,J=5 Hz).

REFERENCE EXAMPLE 33

4-Ethoxy-9-hydroxy-3-methyl-2,3-cycloheptenopyridine 7.6 ml of Acetic anhydride is added to 1.12 g (5.00 mmol) of 4-ethoxy-3-methyl-2,3-cycloheptenopyridine-N-oxide, and the mixture is stirred at 90° C. for 1 hour and 40 minutes. After cooling, the reaction mixture is poured into ice water and neutralized with a 20% aqueous sodium hydroxide solution, and the mixture is extracted with chloroform. The chloroform layer is washed successively with water and saturated saline and dried over anhydrous magnesium sulfate, and the solvent is distilled away under reduced pressure. The resulting residue is dissolved in 24 ml of methanol, 14 ml of a 10% aqueous sodium hydroxide solution is added under ice cooling, and the mixture is stirred at room temperature for 1 hour and 46 minutes. The reaction mixture is poured into ice water and extracted with methylene chloride. The methylene chloride layer is washed successively with water and saturated saline and dried over anhydrous magnesium sulfate, and the solvent is distilled away under reduced pressure. The resulting residue is purified by silica gel column chromatography (chloroformmethanol 40:1) to obtain 1.02 g (91.9%) of 4-ethoxy-9-hydroxy-3-methyl-2,3-cycloheptenopyridine as pale brown oily sustance.

IR$\nu$ max(neat): 3364, 2974, 2926, 2854, 1590, 1569, 1443, 1425, 1395, 1290, 1263, 1230, 1209, 1098, 1047 918, 753 cm$^{-1}$.

NMR(CDCl$_3$)$\delta$: 1.00–2.53(7H,m), 1.43(3H,t,J=7 Hz), 2.21(3H,s), 3.10–3.46 (1H,m), 3.84(2H,q,J=7 Hz), 4.67 (1H,d,J=10 Hz), 5.88(1H,bs), 8.10(1H,s).

REFERENCE EXAMPLE 34

9-Hydroxy-4-methoxy-2,3-cycloheptenopyridine 910 mg (3.87 mmol) of 9-acetoxy-4-methoxy-2,3-cycloheptenopyridine is dissolved in methanol, a 10% aqueous sodium hydroxide solution is added, and after stirring at room temperature for 1 hour, the mixture is refluxed at 80° C. for 10 minutes. After cooling, the methanol is distilled away under reduced pressure, and the resulting residue is extracted with methylene chloride. The methylene chloride layer is washed with staturated saline and dried over anhydrous magnesium sulfate, and the solvent is distilled away under reduced pressure. The resulting solid residue is recrystallized from ether-n-hexane to obtain 550 mg (73.5%) of 9-hydroxy-4-methoxy-2,3-cycloheptenopyridine as yellowish prismatic crystals having a melting point of 119° to 120° C.

IR$\nu$ max(neat): 3312, 2984, 2982, 2852, 1590, 1478, 1450, 1398, 1284, 1260, 1050, 866, 824, 526 cm$^{-1}$.

NMR(CDCl$_3$)$\delta$:0.80–2.34(7H,m), 3.22–3.56 (1H,m), 3.84(3H,s), 4.72(1H,d,J=11 Hz), 6.69(1H,d,J=6 Hz), 8.23 (1H,d,J=6 Hz).

The compounds of the following Reference examples 35 and 36 are obtained in the same manner as above.

REFERENCE EXAMPLE 35

9-Hydroxy-2,3-cycloheptenopyridine

Faintly yellow oily substance
Yield: 64.9%

IR$\nu$ max(neat): 3372, 2982, 2852, 1584, 1454, 1440, 1406, 1062, 796, 772 cm$^{-1}$.

NMR(CDCl$_3$)$\delta$: 0.85–3.02(7H,m), 4.48–4.95 (1H,m), 5.88(1H,bs), 6.93–7.57 (2H,m), 8.32(1H,d,J=5 Hz).

REFERENCE EXAMPLE 36

4-Chloro-9-hydroxy-2,3-cycloheptenopyridine

Colorless crystalline powder
Yield: 97.6%

IR$\nu$ max(KBr): 3400, 2924, 2852, 1564, 1454, 1422, 1380, 1064, 840, 778 cm$^{-1}$.

NMR(CDCl$_3$)$\delta$: 0.80–2.70(7H,m), 3.47(1H,dd,J =11 Hz,J=6 Hz), 4.80(1H,d,J=11 Hz), 5.75(1H,bs), 7.18(1H,d,J=5 Hz), 8.17(1H,d,J=5 Hz).

REFERENCE EXAMPLE 37

9-Chloro-4-ethoxy-3-methyl-2,3-cycloheptenopyridine

In a stream of argon, 1.02 g (4.59 mmol) of 4-ethoxy-3-methyl-9-hydroxy-2,3-cycloheptenopyridine is dissolved in 6.5 ml of chloroform, 1.66 ml (23.0 mmol) of thionyl chloride is added dropwise with stirring at −12° C., and after stirring at the same temperature for 30 minutes, the mixture is stirred at room temperature for 16 hours. The reaction mixture is poured in ice water, neutralized with a saturated aqueous sodium hydrogen carbonate and extracted with chloroform. The chloroform layer is washed successively with water and saturated saline and dried over anhydrous magnesium sulfate, and the solvent is distilled away under reduced pressure to obtain crude 9-chloro-4-ethoxy-3-methyl-2,3-cycloheptenopyridine as a pale brown oily substance.

IR$\nu$ max(neat): 2976, 2928, 2860, 1564, 1460, 1384, 1336, 1286, 1266, 1228, 1210, 1110, 1082, 1054, 1044, 1026, 958, 752, 736 cm$^{-1}$.

NMR(CDCl$_3$)$\delta$: 1.20–2.56(6H,m), 1.41(3H,t,J=7 Hz), 2.21(3H,s), 2.60–3.36 (2H,m), 3.81(2H,q,J=7 Hz), 5.41 (1H,d,J=5 Hz), 8.06(1H,s).

REFERENCE 38

9-Bromo-2,3-cycloheptenopyridine 1.13 g (8.16 mmol) of 9-hydroxy-2,3-cycloheptenopyridine is dissolved in 10 ml of dry benzene, 0.28 ml of phosphorus tribromide is added dropwise under ice cooling and stirring, and the mixture is stirred overnight at room temperature. After the reaction, ice water is added for cooling, and the mixture is neutralized with 1N sodium hydroxide and extracted with methylene chloride. The methyhlene chloride layer is washed with saturated saline and dried over anhydrous magnesium sulfate, and the solvent is distilled away under reduced pressure. The resulting residue is prified by silica gel column chromatography (chloroform-methanol 200:1) to obtain 391 mg (21.3%) of 9-bromo-2,3-cycloheptenopyridine as yellowish oily substance.

IR$\nu$ max(neat): 3045, 2928, 2856, 1754, 1452, 1440, 1186, 964, 792, 776 698, 682 cm$^{-1}$.

NMR(CDCl$_3$)$\delta$: 1.02–3.50(8H,m), 5.58(1H,d,J= 5 Hz), 6.94–7.67(2H,m), 8.28 (1H,d,J=5 Hz).

The compounds of Table-3 can be halogenated in the same manner as in the above Reference examples 33 to 37.

EXAMPLE 1

9-(5-Methoxybenzimidazole-1-yl)thio-2,3-cycloheptnopyridine 303 mg (1.68 mmol) of 2-mercapto-5-methoxybenzimidazole is dissolved in an aqueous sodium hydroxide solution (wherein 80 mg of sodium hydroxide is dissolved in 1.4 ml of water) and 10 ml of methanol, 379 mg (1.68 mmol) of 9-bromo-2,3-cycloheptenopyridine is added thereto with stirring at room temperature, and the mixture is refluxed for 1.5 hours. After cooling, the methanol is distilled away under reduced pressure, and the residue is extracted with methylene chloride. The methylene chloride layer is washed with saturated saline and dried over anhydrous magnesium sulfate, and the solvent is distilled away under reduced pressure. The resulting oily residue is purified by silica gel column chromatography (chloroform) and recrystallized from chloroform-n-hexane to obtain 355 mg (64.9%) of 9-(5-methoxybenzimidazole-2-yl)thio-2,3-cycloheptenopyridine as colorless granular crystals having a melting point of 157° to 158° C.

IR$\nu$ max(KBr): 2924, 1625, 1452, 1434, 1396, 1158 cm$^{-1}$.

NMR(CDCl$_3$)$\delta$: 1.34–2.45(6H,m), 2.60–3.34 (2H,m), 5.08(1H,d,J=6 Hz), 6.63–7.56(5H,m), 8.35(1H,d,J=5 Hz).

The compound of the following Example 2 is obtained in the same manner as above.

EXAMPLE 2

9-(Benzimidazole-2-yl)thio-2,3-cycloheptenopyridine

Colorless minute needle crystals
Melting point: 281° to 282° C.
Yield 63.4%

IR$\nu$ max(KBr): 2924, 2852, 2788, 2696, 2632, 1454, 1438, 1398, 1348, 1270, 746 cm$^{-1}$.

NMR(CDCl$_3$-DMSO-D$_6$)δ: 1.53–2.46(6H,m), 3.35–3.67(2H,m), 5.29–5.65(1H,br), 6.98–7.77(6H,m), 8.30(1H,d,J=5 Hz).

EXAMPLE 3

9-(5-nitrobenzimidazole-2-yl)thio-2,3-cycloheptenopyridine 327 mg (2 mmol) of 9-hydroxy-2,3-cycloheptenopyridine is dissolved in 3 ml of chloroform from which ethanol is removed, 0.73 ml (10 mmol) of thionyl chloride is added dropwise with cooling at −15° C., and the mixture is stirred overnight at room temperature. After the reaction, the solvent is distilled away under reduced pressure, the residue is dissolved in methylene chloride, the solution is washed with saturated sodium hydrogen carbonate, and the solvent is distilled away to obtain crude 9-chloro-2,3-cycloheptenopyridine.

The crude 9-chloro-2,3-cycloheptenopyridine is dissolved in 5 ml of ethanol, the solution is added to ethanol (10 ml)—an aqueous sodium hydroxide solution (wherein 120 mg of sodium hydroxide is dissolved in 2 ml of water), containing 303 mg (1.68 mmol) of 2-mercapto-5-nitrobenzimidazole, and the resulting mixture is refluxed for 21 hours. After the reaction, the ethanol is distilled away under reduced pressure, and the resulting residue is extracted with chloroform. The chloroform layer is washed with saturated saline and dried over anhydrous magnesium sulfate, and the solvent is distilled away under reduced pressure. The resulting oily residue is purified by silica gel column chromatography (chloroform) and recrystallized from ethyl acetate-n-hexane to obtain 359 mg (52.7%) of 9-(5-nitrobenzimdazole-2-yl)thio-2,3-cycloheptenopyridine as colorless granular crystals having a melting point of 222° to 223° C.

IRν max(KBr): 3072, 2928, 2852, 1514, 1452, 1432, 1332, 1276, 1066, 736 cm$^{-1}$.

NMR(CDCl$_3$)δ: 1.54–3.34(8H,m), 5.17(1H,bs), 7.02–7.68(3H,m), 7.92–8.48 (3H,m).

The compounds of the following Examples 4 to 7 are obtained in the same manner as above.

EXAMPLE 4

9-(5-Chlorobenzimidazole-2yl)thio-2,3-cycloheptenopyridine

Yellowish candy-like substance
Yield: 78.8%
IRν max(neat): 3056, 2932, 2856, 1452, 1432, 1406, 1332, 1266, 1060, 992 754 cm$^{-1}$.
NMR(CDCl$_3$)δ: 1.42–3.43(8H,m), 5.12(1H,bs), 6.94–8.85(5H,m), 8.35(1H,d,J=5 Hz).

EXAMPLE 5

9-(5-Fluorobenzimidazole-2-yl)thio-2,3-cycloheptenopyridine

Colorless powder
Melting point: 202° to 203° C.
Yield: 53.6%
IRν max(KBr): 3036, 2924, 2848, 1482, 1436, 1396, 1345, 1262, 1216, 1142 988, 960, 836, 802 cm$^{-1}$.
NMR(CDCl$_3$)δ: 1.30–2.53(6H,m), 2.55–3.43 (2H,m), 4.95–5.33(1H,m), 6.66–7.68(5H,m), 8.32(1H,d,J=3 Hz).

EXAMPLE 6

9-(5-Methylbenzimidazole-2-yl)thio-2,3-cycloheptenopyridine

Pale yellow powder
Melting point: 207° to 208.5° C.
Yield: 44.9%
IRν max(KBr): 2924, 2848, 2784, 2616, 1434, 1390, 1276, 800 cm$^{-1}$.
NMR(CDCl$_3$)δ: 1.40–2.43(6H,m), 2.41(3H,s), 2.60–3.40(2H,m), 4.97–5.23 (1H,m), 6.76–7.62(5H,m), 8.35 (1H,d,J=4 Hz).

EXAMPLE 7

9-(5-Trifluoromethylbenzimidazole-2-yl)thio-2,3-cycloheptenopyridine

Pale yellow amorphous powder
Yield: 53.1%
IRν max(KBr): 2932, 1452, 1432, 1328, 1280, 1246, 1160, 1116, 1050, 756 cm$^{-1}$.
NMR(CDCl$_3$)δ: 1.43–2.50(6H,m), 2.56–3.23 (2H,m), 5.23(1H,bs), 6.96–7.93 (5H,m), 8.17–8.53(1H,m).

EXAMPLE 8

9-(5-Methoxybenzimidazole-2-yl)thio-4-methoxy-2,3-cycloheptenopyridine 700 mg (3.62 mmol) of 9-hydroxy-4-methoxy-2,3-cycloheptenopyridine is dissolved in 6 ml of chloroform from which ethanol is removed, 1.3 ml (17.9 mmol) of thionyl chloride is added dropwise under cooling at −15° C., and the mixture is stirred overnight at room temperature. After the reaction, the solvent is distilled away under reduced pressure, the residue is dissolved in methylene chloride, the resulting solution is washed with saturated sodium hydrogen carbonate, and the solvent is distilled away to obtain crude 9-chloro-4-methoxy-2,3-cycloheptenopyridine.

The crude 9-chloro-4-methoxy-2,3-cycloheptenopyridine is dissolved in 5 ml of ethanol, the solution is added to previously prepared ethanol (2 ml)—an aqueous sodium hydroxide solution (wherein 290 mg of sodium hydroxide is dissolved in 4.5 ml of water), containing 783 mg (4.34 mmol) of 2-mercapto-5-methoxybenzimidazole, and the resulting mixture is refluxed for 4.5 hours. After the reation, the ethanol is distilled away under reduced pressure, and the resulting residue is extracted with methylene chloride. The methylene chloride layer is washed with saturated saline and dried over magnesium sulfate, and the solvent is distilled away under reduced pressure. The resulting solid residue is purified by alumina column chromatography (ethyl acetate-n-hexane 1:3) to obtain 940 mg (73.0%) of 9-(5-methoxylenzimidazole-2-yl)thio-4-methoxy-2.3-cycloheptenopyridine as colorless amorphous powder.

IRν max(KBr): 2924, 2840, 1578, 1432, 1288, 1152, 814 cm$^{-1}$.
NMR(CDCl$_3$)δ: 1.22–2.39(6H,m), 2.74–3.36 (2H,m), 3.79, 3.82(each 3H,s), 5.06(1H,t,J=4 Hz), 6.62–7.60 (3H,m), 6.70(1H,d,J=6 Hz), 8.25 (1H,d,J=6 Hz).

The compounds of the following Examples 9 to 11 are obtained in the same manner as above.

EXAMPLE 9

9-(Benzimidazole-2-yl)thio-4-methoxy-2,3-cycloheptenopyridine

Colorless powder

Melting point: 176° to 179° C.
Yield: 69.8%
IRν max(KBr): 3044, 2920, 1578, 1436, 1406, 1156, 810, 752 cm$^{-1}$.
NMR(CDCl$_3$)δ: 1.14(6H,m), 2.45-3.47(2H,m), 3.82(3H,s), 5.10(1H,t,J=4 Hz), 6.68(1H,d,J=6 Hz), 6.97-7.30 (2H,m), 7.30-7.63(2H,m), 8.24 (1H,d,J=6 Hz).

EXAMPLE 10

9-(5-Flurobenzimidazole-2-yl)thio-4-methoxy-2,3-cycloheptenopyridine

Yellowish powder
Melting point: 93° to 95° C.
Yield: 74.8%
IRν max(KBr): 3045, 2976, 2928, 1628, 1580, 1438, 1290, 1134, 1052, 838 cm$^{-1}$.
NMR(CDCl$_3$)δ: 1.15-2.43(6H,m), 2.53-3.50 (2H,m), 3.83(3H,s),5.08(1H,bs), 6.54-7.52(3H,m), 6.72(1H,d,J=6 Hz), 8.25(1H,d,J=6 Hz).

EXAMPLE 11

9-(5-Methyoxybenzimidazole-2-yl)thio-4-chloro-2,3-cycloheptenopyridine

Colorless powder
Melting point: 113° to 116° C.
Yield: 63.4%
IRν max(KBr): 2928, 1625, 1560, 1490, 1456, 1432, 1404, 1346, 1200, 1154, 834 cm$^{-1}$.
NMR(CDCl$_3$)δ: 1.40-2.52(6H,m), 3.07-3.38 (2H,m),3.80(3H,s), 5.06-5.33 (1H,m), 6.63-7.60(4H,m), 8.20 (1H,d,J=5 Hz).

EXAMPLE 12

9-(Benzimidazole-2-yl)thio-4-(2-hydroxyethoxy)-2,3-cycloheptenopyridine

In a stream of argon, 1.48 g (3.32 mmol) of 9-(benzimidazole-2-yl)thio-4-(2-benzyloxyethoxy)-2,3-cycloheptenopyridine is suspended in 7.5 ml of methylene chlordie, 7.5 ml of dimethyl sulfide is added and dissolved under ice cooling and stirring, 3.75 ml (30.5 mmol) of a trifluoroborane-ether complex is added dropwise, and the resulting mixture is stirred for 30 minutes under ice cooling and further for 12 hours at room temperature. After completion of the reaction, the reaction mixture is poured into ice water, and the resulting mixture is made weakly alkaline with potassium carbonate and extracted with chloroform. The chlorform layer is washed successively with water and saturated saline and dried over anhydrous magnesium sulfate, and the solvent is distilled away under reduced pressure. The resulting residue is separated and purified by silica gel column chromatography (chloroform-methanol 30:1) to obtain 1.18 g (99.8%) of 9-(benzimidazole-2-yl)thio-4-(2-hydroxyethoxy)-2,3-cycloheptenopyridine as colorless amorphous powder.

IRν max(KBr): 3154, 3064, 2926, 2854, 1581, 1470, 1437, 1407, 1350, 1290, 1269, 1230, 1092, 1053, 903, 813, 741 cm$^{-1}$.
NMR(CDCl$_3$)δ: 1.20-3.40((8H,m), 3.95-4.35 (4H,m), 4.96-5.20(1H,m), 6.70 (1H,d,J=6 Hz), 6.99-7.55(4H,m), 8.22(1H,d,J=6 Hz).

EXAMPLE 13

4-(2-Acetoxyethoxy)-9-(benzimidazole-2-yl)thio-2,3-cycloheptenopyridine

In a stream of argon, 573 mg (1.44 mmol) of 9-(benzimidazole-2-yl)thio-4-(2-hydroxyethoxy)-2,3-cycloheptenopyridine is dissolved in 6 ml of methylene chloride, 0.46 ml (5.76 mmol) of pyridine is added dropwise with stirring at room temperature and successively 0.27 ml (2.88 mmol) of acetic anhydride is added dropwise, and the resulting mixture is stirred at room temperature for 14 hours and 30 minutes. After cooling, the reaction mixture is poured into ice water, followed by extraction with chloroform. The chloroform layer is washed successively with water and saturated saline and dried over anhydrous magnesium sulfate, and the solvent is distilled away under reduced pressure. The resulting residue is purified by silica gel column chromatography (chloroform-methanol 30:1). The resulting oily substance is dissolved in methylene chloride, 7.28 g of silica gel is added, the mixture is stirred at room temperature for 1 hour, the silica gel is filtered off, and then the methylene chloride is distilled away under reduced pressure to obtain 520 mg (90.9%) of 9-(benzimidazole-2-yl)thio-4-(2-acetoxyethoxy)-2,3-cycloheptenopyridine as a colorless oily substance.

IRν max(Neat): 2928, 1740, 1580, 1470, 1452, 1438, 1406, 1290, 1268, 1228, 1094, 1058, 908, 736, 648, 604 cm$^{-1}$.
NMR(CDCl$_3$)δ: 1.18-2.42(6H,m), 2.70(3H,s), 2.56-3.41(2H,m), 4.06-4.30 (2H,m), 4.30-4.54(2H,m), 4.99-5.22(1H,m), 6.69(1H,d,J=6 Hz), 6.96-7.26(2H,m), 7.30-7.62 (2H,m), 8.24(1H,d,J=6 Hz).

EXAMPLE 14

4-Ethoxy-9-(5-methoxybenzimidazole-2-yl)thio-3-methyl-2,3-cycloheptenopyridine

Crude 9-chloro-4-ethoxy-3-methyl-2,3-cycloheptenopyridine (4.95 mmol) is dissolved in 16 ml of ethanol, 892 mg (4.95 mmol) of 5-methoxy-2-mercaptobenzimidazole and 16 ml of a 20% aqueous sodium hydroxide solution are added, and the mixture is refluxed with heating for 20 hours. After cooling, the solvent is distilled away under reduced pressure and the residue is extracted with chloroform. The chloroform layer is washed successively with a saturated aqueous sodium hydrogen carbonate solution, water and saturated saline and dried over anhydrous magnesium sulfate, and the solvent is distilled away under reduced pressure. The resulting residue is subjected to active alumina column chromatography (ethy acetate:hexane 2:3→ethyl acetate→ethyl acetate:methanol 100:1) to obtain 799 mg (42.1%) of 4-ethoxy-9-(5-metoxybenzimidazole-2-yl)thio-3-methyl-2,3-cycloheptenopyridine as colorless amorphous powder.

IRν max(KBr): 2976, 2924, 2852, 1626, 1450, 1398, 1344, 1288, 1268, 1228, 1200, 1154, 1052, 1026, 960, 838, 802 cm$^{-1}$.
NMR(CDCl$_3$)δ: 1.10-2.40(6H,m), 1.43(3H,t,J=7 Hz), 2.23(3H,s), 2.65-3.33 (2H,m), 3.65-4.03(2H,m), 3.81 (3H,s), 4.93-5.16(1H,m), 6.65-7.65(3H,m), 8.14(1H,s).

EXAMPLE 15

9-[1-(Benzyloxycarbonyl)benzimidazole-2-yl]thio-4-methoxy-2,3-cycloheptenopyridine In a stream of argon, 520 mg (1.60 mmol) of 9-(benzimidazole-2-yl)thio-4-methoxy-2,3-cycloheptenopyridine is dissolved in 10 ml of THF, 215 mg (1.90 mmol) of potassium t-butoxide (t-Buok) dissolved in 8 ml of THF is added dropwise under ice cooling and stirring, and the mixture is stirred at room temperature for 20 minutes. Then, 607 mg (3.20 mmol) of carbobenzoxy chloride dissolved in 2 ml of THF is added dropwise, and the mixture is stirred at room temperature for 30 minutes. After completion of the reaction, a saturated aqueous ammonium chloride solution is added to the reaction mixture, followed by extraction with methylene chloride. The methylene chloride layer is washed successively with water and saturated saline and dried over anhydrous magnesium sulfate, and the solvent is distilled away under reduced pressure. The resulting residue is crystallized from chloroform-hexane to obtain 657 mg (89.5%) of 9-[1-(benzyloxycarbonyl)benzimidazole-2-yl]thio-4-methoxy-2,3-cycloheptenopyridine as colorless powder having a melting point of 181° to 184° C.

IR$\nu$ max(KBr): 3430, 2910, 1736, 1576, 1466, 1450, 1392, 1332, 1294, 1280, 1254, 1194, 1078 cm$^{-1}$.

NMR(CDCl$_3$)$\delta$:1.36–2.94(7H,m), 3.06–3.33 (1H,m), 3.82(3H,s), 5.50(2H,s), 5.66(1H,d,J=9.0 Hz), 6.65(1H,d,J =7.5 Hz), 6.97–7.86(9H,m), 8.23 (1H,d,J=7.5 Hz).

EXAMPLE 16

9-[1-(hydroxymethyl)benzimidazole-2-yl]thio-4-methoxy-2,3-cycloheptenopyridine 958 mg (2.95 mmol) of 9-(benzimidazole-2-yl)thio-4-methoxy-2,3-cycloheptenopyridine is dissolved in 16 ml of acetonitrile and 16 ml of methylene chloride, and under stirring 0.36 ml (4.42 mmol) of 37% formaldehyde dissolved in 1 ml of acetonitrile is added dropwise. The mixture is then stirred for 30 minutes and further at 70° C. for 45 minutes. The reaction mixture is poured into ice water, followed by extraction with methylene chloride. The methylene chloride layer is washed successively with water and saturated saline and dried over anhydrous magnesium sulfate, and the solvent is distilled away under reduced pressure. The resulting residue is crystallized from methylene chloride-hexane to obtain 676 mg (64.6%) of 9-[1-(hydroxymethyl)benzimidazole-2-yl]thio-4-methoxy-2,3-cycloheptenopyridine as colorless powder having a melting point of 136° to 138° C. The mother liquor is evaporated under reduced pressure, and the resulting residue is crystallized from methylene chloride-ether-hexane to obtain 246 mg (23.5%) of the above compound (total yield 88.1%).

IR$\nu$ max(KBr): 3132, 2968, 2936, 1578, 1474, 1466, 1428, 1366, 1330, 1304, 1288, 1250, 1136, 1102, 1082 cm$^{-1}$.

NMR(CDCl$_3$)$\delta$: 1.33–3.20(8H,m), 3.80(3H,s), 4.81–5.16(1H,m), 5.73(2H,q,J= 9 Hz), 6.60(1H,d,J=7.5 Hz), 7.03–7.86(4H,m), 8.00(1H,d,J=7.5 Hz).

EXAMPLE 17

9-[1-(t-Butoxycarbonylmethoxymethyl)benzimidazole-2-yl]thio-4-methoxy-2,3-cycloheptenopyridine In a stream of argon, 48 mg (1.20 mmol) of 60% sodium hydride is suspended in 5 ml of THF, and under ice cooling and stirring, 355 mg (1.00 mmol) of 9-[1-(hydroxymethyl)benzimidazole-2-yl]thio-4-methoxy-2,3-cycloheptenopyridine dissolved in 5 ml of THF is dropwise added by portions. The resulting mixture is stirred at room temperature for 45 minutes. Then, under ice cooling and stirring, t-butoxycarbonyl bromide dissolved in 2 ml of THF is added dropwise, and the mixture is stirred at room temperature for 16 hours. After the reaction, the reaction mixture is poured into a saturated aqueous ammonium chloride solution, followed by extraction with methylene chloride. The methylene chloride layer is washed successively with water and saturated saline and dried over anhydrous magnesium sulfate, and the solvent is distilled away under reduced pressure to obtain 427 mg (91.2%) 9-[1-(t-butoxycarbonylmethoxymethyl)benzimidazole-2-yl]thio-4-methoxy-2,3-cycloheptenopyridine IR$\nu$ max(KBr): 2976, 2928, 1744, 1626, 1578, 1474, 1444, 1368, 1334, 1314, 1282, 1232, 1156, 1114, 1092 cm$^{-1}$.

NMR(CDCl$_3$)$\delta$: 1.40(9H,s), 1.60–2.80(7H,m), 3.16–3.46(1H,m), 3.83(3H,s) 4.83(2H,s), 5.50–5.75(1H,m), 5.70(2H,s), 6.67(1H,d,J=7.5 Hz), 7.04–7.80(4H,m), 8.10–8.28 (1H,d,J=7.5 Hz).

EXAMPLE 18

9-[pyrido[2,3-d]imidazole-2-yl]thio-2,3-cycloheptenopyridine

Crude 9-chloro-2,3-cycloheptenopyridine (9.15 mmol) is dissolved in 29 ml of ethanol, 1.38 g (9.15 mmol) of 2-mercaptopyrido [2,3-d] imidazole and 29 ml of a 20% aqueous sodium hydroxide solution are added thereto, and the mixture is refluxed with heating for 20 hours. After cooling, the solvent is distilled away under reduced pressure, and the residue is extracted with chloroform. The chloroform layer is washed successively with a saturated aqueous sodium hydrogen carbonate solution, water and saturated saline, and dried over anhydrous magnesium sulfate, and the solvent is distilled away under reduced pressure. The resulting residue is subjected to activated alumina column chromatography (ethyl acetate:hexane 2:3→ethyl acetate→ethyl acetate:methanol 100:1) to obtain 700 mg (25.8%) of 9-[pyrido[2,3-d]imidazaole-2-yl]thio-2,3-cycloheptenopyridine as colorless amorphous powder.

IR$\nu$ max(KBr): 2921, 1452, 1439, 1393, 1268, 768, 753 cm$^{-1}$.

NMR(CDCl$_3$)$\delta$: 1.39–2.60(6H,m), 2.60–3.30 (2H,m), 5.13–5.33(1H,m), 6.97–7.30(2H,m), 7.31–7.60(1H,m), 7.56–7.92(1H,m), 8.15–8.50 (2H,m).

The compounds in Table-4 are obtained in the same manner as in Examples 1 to 18.

TABLE 4

[Structure: bicyclic compound with cycloheptane fused to pyridine (with R substituent), linked via S to imidazole bearing R² and R³, with R¹ substituent]

| Example No. | R | R¹ | R² | R³ | A | Melting point (yield) | IR νcm⁻¹ | NMR(CDCl₃)δ |
|---|---|---|---|---|---|---|---|---|
| 19 | H | OEt | H | H | CH | Colorless amorphous powder (74.2%) | (KBr) 3432, 2976, 2924, 1464, 1438, 1290, 1268, 1232, 1088. | 1.43(3H, t, J=7.5Hz), 1.66–3.32(8H, m), 4.03(2H, q, J=7.5Hz), 5.19(1H, t, J=6Hz), 6.65(1H, d, J=9Hz), 6.96–7.66(4H, m), 8.22(1H, d, J=9Hz) |
| 20 | H | O-n-Bu | H | H | CH | Colorless powder (55.8%) 65–70° C. | (KBr) 3429, 3064, 2928, 1580, 1460, 1438, 1288, 1268, 1088. | 0.96(3H, t, J=7.5Hz), 1.12–2.43(10H, m), 2.60–3.31(2H, m), 3.96(2H, t, J=7.5Hz), 5.18(1H, t, J=6Hz), 6.66(1H, d, J=7.5Hz), 6.86–8.64(4H, m), 8.22(1H, d, J=7.5Hz) |
| 21 | H | [4-methylphenoxy] | H | H | CH | Palely yellow needle crystal (55.4%) 222–223° C. | (KBr) 3430, 2928, 1576, 1504, 1460, 1438, 1398, 1348, 1332, 1270, 1250, 1204, 1162. | 1.36–3.55(8H, m), 2.33(3H, s), 5.03–5.30 (1H, m), 6.50(1H, d, J=7.5Hz), 6.84(2H, d, J=7.5Hz), 6.96–7.66(6H, m), 8.13(1H, d, J=7.5Hz) |
| 22 | H | [cyclopropylmethoxy] | H | H | CH | Colorless powder (46.4%) 159–160° C. | (KBr) 3460, 3080, 3032, 2960, 2924, 1582, 1462, 1450, 1430, 1404, 1350, 1272, 1042, 1008. | 0.13–0.76(4H, m), 1.10–1.64(1H, m), 1.66–3.46(8H, m), 3.83(1H, d, J=7.5Hz), 5.10(1H, t, J=6Hz), 6.65(1H, d, J=7.5Hz), 6.97–7.64(4H, m), 8.22(1H, d, J=7.5Hz) |
| 23 | H | [tetrahydrofurfuryloxy] | H | H | CH | Colorless amorphous powder (82.9%) | (KBr) 2972, 2928, 2860, 1578, 1438, 1406, 1346, 1290, 1268, 1230, 1082, 1050. | 1.36–2.53(10H, m), 2.64–3.36(1H, m), 3.73–4.36(5H, m), 5.08(1H, t, J=6Hz), 6.70(1H, d, J=7.5Hz), 6.94–7.76(4H, m), 8.23(1H, d, J=7.5Hz) |
| 24 | H | OCH₃ | H | CH₂OCOCH₃ | CH | Colorless powder (61.1%) 160–162° C. | (KBr) 2924, 1750, 1578, 1472, 1440, 1352, 1280, 1260, 1212, 1052, 1018. | 1.63–2.85(7H, m), 2.03(3H, s), 3.07–3.46 (1H, m), 3.83(3H, s), 5.64(1H, d, J=10.5 Hz), 6.15(2H, d, d, J=30Hz, J=30Hz), 6.67 (1H, d, J=7.5Hz), 7.06–7.76(4H, m), 8.23 (1H, d, J=7.5Hz) |
| 25 | H | OCH₃ | H | CH₂OCH₃ | CH | Colorless amorphous powder (71.0%) | (KBr) 2928, 2852, 1578, 1432, 1334, 1283, 1268, 1112, 1092, 1056. | 1.56–2.86(7H, m), 3.10–3.46(1H, m), 3.29 (3H, s), 3.83(3H, s), 5.52(2H, s), 5.68, (1H, d, J=9Hz), 6.66(1H, d, J=7.5Hz), 7.06–7.78(4H, m), 8.22(1H, d, J=7.5Hz) |
| 26 | H | OCH₃ | H | CH₂OEt | CH | Colorless candy-like substance (66.8%) | (neat) 2976, 2928, 2856, 1578, 1474, 1434, 1394, 1264, 1092, 1056, 942. | 1.43(3H, t, J=9Hz), 1.62–2.43(7H, m), 2.46–2.85(1H, m) 3.50(2H, s), 5.55(2H, s), 5.67(1H, d, 3.80(3H, s), |

TABLE 4-continued

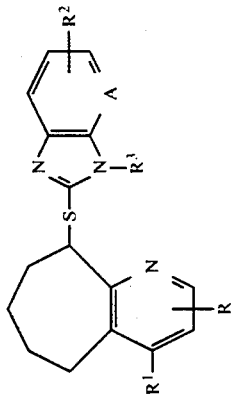

| Example No. | R | R¹ | R² | R³ | A | Melting point (yield) | IR νcm⁻¹ | NMR(CDCl₃)δ |
|---|---|---|---|---|---|---|---|---|
| 27 | H | OCH₃ | H | CH₂O(CH₂)₂OCH₃ | CH | Colorless candy-like substance (91.7%) | (neat) 2924, 2852, 1578, 1472, 1332, 1282, 1264, 1134, 1090, 1056, | J=10.5Hz), 6.65(1H, d, J=7.5Hz), 7.06-7.75 (4H, m), 8.22(1H, d, J=7.5Hz) |
| 28 | H | OCH₃ | H | COO(CH₂)₂OCH₃ | CH | Palely yellow powder (90.6%) 150-151° C. | (KBr) 2920, 2848, 1746, 1578, 1452, 1406, 1384, 1332, 1264, 1192, 1138, 1076, | 1.54-2.86(8H, m), 3.14-3.84(4H, m), 3.29 (3H, s), 3.81(3H, s), 3.50-3.81(1H, m), 3.51(2H, m), 6.64(1H, d, J=7.5Hz), 7.05-7.73(4H, m), 8.11(1H, m) 1.62-2.94(8H, m), 3.43(3H, s), 3.76(2H, t, J=6Hz), 3.82(3H, s), 4.62(2H, t, J=6Hz), 5.53-5.83(1H, m), 6.65(1H, d, J=7.5Hz), 7.04-7.98(4H, m), 8.22(1H, d, J=7.5Hz) |
| 29 | H | OCH₂CF₂CF₃ | H | H | CH | Colorless amorphous powder (58.1%) | (KBr) 2928, 1578, 1440, 1404, 1350, 1294, 1268, 1198, 1152, 1100, 740 | 1.13-2.40(6H, m), 2.70-3.38(2H, m), 4.46 (2H, t, J=12Hz), 5.20(1H, t, J=4Hz), 6.69 (1H, t, J=5Hz), 7.00-7.78(4H, m), 8.33 (1H, d, J=5Hz) |
| 30 | H | OCH₂CF₂CF₂H | H | H | CH | Colorless amorphous powder (51.7%) | (KBr) 3064, 2929, 2856, 1578, 1470, 1454, 1438, 1404, 1348, 1312, 1290, 1268, 1228, 1200, 1106, 1062, 942, 836, 810, 742. | 1.10-2.42(6H, m), 2.73-3.35(2H, m), 4.38 (2H, m), 5.18(1H, br), 5.38, 5.98, 6.57 (1H, t×3, J=3Hz), 6.70(1H, d, J=6Hz), 7.00-7.75(4H, m), 8.32(1H, d, J=6Hz) |
| 31 | H | OCH₂Ph | H | H | CH | Colorless amorphous powder (65.0%) | | 1.15-2.45(6H, m), 2.63-3.40(2H, m), 5.05(2H, s), 5.20(1H, t, J=4Hz), 6.70 (1H, d, J=5Hz), 7.10-7.95(4H, m), 7.31 (5H, s), 8.21(1H, d, J=5Hz) |
| 32 | H | SCH₂CH₂CH₃ | H | H | CH | Colorless amorphous powder (42.0%) | | 1.08(3H, t, J=7Hz), 1.20-3.68(12H, m), 5.20(1H, br), 6.97(1H, d, J=5Hz), 7.00-7.95(4H, m), 8.21(1H, d, J=5Hz) |
| 33 | H | ![morpholine] | H | H | CH | Colorless powder (56.4%) 215-217° C. | (KBr) 2960, 2924, 2852, 1580, 1446, 1420, 1394, 1342, 1270, 1252, 1116, 988, 904, 740. | 1.08-2.47(6H, m), 2.73-3.35(6H, m), 3.67-4.05(4H, m), 5.04-5.25(1H, m), 6.80(1H, d, J=6Hz), 7.00-7.76(4H, m), 8.26(1H, d, J=6Hz) |
| 34 | H | OCH₂CH₂OCH₃ | 5-F | H | CH | Colorless powder (43.6%) 141-142° C. | (KBr) 2928, 2856, 1582, 1474, 1432, 1404, 1346, 1286, 1260, 1230, 1196, 1130, 1110, 1084, 1056, 1036, 966, 952, 800, | 1.13-2.53(6H, m), 2.63-3.30(2H, m), 3.42 (3H, s), 3.63-3.86(2H, m), 4.02-4.24(2H, m), 4.98-5.20(1H, m), 6.72(1H, d, J=7Hz), 6.76-7.57(3H, m), 8.22(1H, d, J=7Hz) |
| 35 | H | OCH₃ | 5,6-OCH₃ | H | CH | Colorless powder | (KBr) 2932, 1578, 1488, 1472, | 1.03-2.35(6H, m), 2.63(2H, m), 3.84(3H, s), |

TABLE 4-continued

| Example No. | R | R¹ | R² | R³ | A | Melting point (yield) | IR νcm⁻¹ | NMR(CDCl₃)δ |
|---|---|---|---|---|---|---|---|---|
| 36 | H | OCH₂CF₃ | H | H | CH | (38.9%) 112–114.5° C. | 1440, 1420, 1398, 1328, 1282, 1196, 1170, 1136. | 3.88(6H, s), 4.86–5.10(1H, m), 6.70(1H, d, J=6Hz), 6.75–7.16(2H, m), 8.25(1H, d, J=6Hz) |
| 37 | H | OCH₂CH=CH₂ | H | H | CH | Palely yellow amorphous powder (47.6%) — | (KBr) 3064, 2856, 1578, 1470, 1454, 1438, 1404, 1348, 1316, 1290, 1264, 1230, 1166, 1138, 1100, 1064, 974. | 1.40–2.50(6H, m), 2.71–3.41(2H, m), 4.37(2H, q, J=9Hz), 5.03–5.26(1H, m), 6.67(1H, d, J=6Hz), 7.00–7.70(4H, m), 8.30(1H, d, J=6Hz) |
| 38 | H | OCH₂CH₂OCH₃ | H | H | CH | Colorless powder (51.6%) 106–108° C. | (KBr) 2924, 2852, 1578, 1468, 1436, 1404, 1346, 1310, 1282, 1268, 1230, 1044, 1016, 930, 816, 740. | 1.05–2.36(6H, m), 2.65–3.36(2H, m), 4.50(2H, d, J=4Hz), 4.96–5.36(2H, m), 5.37(1H, d, J=9Hz), 5.66–6.23(1H, m), 6.63(1H, d, J=5Hz), 6.93–7.30(2H, m), 7.30–7.60(2H, m), 8.18(1H, d, J=5Hz) |
| 39 | H | O(CH₂)₃OCH₃ | H | H | CH | Colorless powder (56.3%) 124–125° C. | (KBr) 2976, 2924, 2856, 1578, 1470, 1438, 1402, 1288, 1266, 1234, 1196, 1128, 1088, 1056, 740. | 1.33–2.35(6H, m), 2.65–3.23(2H, m), 3.39 (3H, s), 3.56–3.83(2H, m), 3.93–4.25(2H, m), 5.02–5.26(1H, m), 6.68(1H, d, J=6Hz), 6.93–7.28(2H, m), 7.28–7.62(2H, m), 8.21(1H, d, J=6Hz) |
| 40 | H | O(CH₂)₂OCH₂Ph | H | H | CH | Colorless amorphous powder (38.5%) — | (KBr) 2924, 2856, 1578, 1460, 1438, 1400, 1286, 1266, 1228, 1116, 1088, 1050, 814, 738. | 1.13–2.40(8H, m), 2.57–3.20(2H, m), 3.30 (3H, s), 3.51(2H, t, J=6Hz), 4.07(2H, t, J=6Hz), 4.99–5.17(1H, m), 6.69(1H, d, J=6Hz), 6.95–7.78(4H, m), 8.22(1H, d, J=6Hz) |
| 41 | H | O(CH₂)₂OPh | H | H | CH | Colorless powder (52.5%) 168–169° C. | (KBr) 2924, 2852, 2804, 1580, 1440, 1400, 1290, 1270, 1120, 750, 732. | 1.10–2.50(6H, m), 2.56–3.53(2H, m), 3.70–3.97(2H, m), 4.00–4.36(1H, m), 4.59(2H, s), 4.98–5.21(1H, m), 6.70(1H, d, J=6Hz), 6.97–7.63(9H, m), 8.24(1H, d, J=6Hz) |
| 42 | H | O(CH₂)₂OCH₂Py | H | H | CH | Colorless amorphous powder (50.9%) — | (KBr) 3056, 2924, 2852, 1598, 1578, 1496, 1470, 1436, 1402, 1288, 1266, 1242, 1172, 1090, 1056, 740, 690. | 1.50–2.50(6H, m), 2.60–3.40(2H, m), 4.33(4H, s), 5.00–5.21(1H, m), 6.66–7.81(9H, m), 8.26(1H, d, J=6Hz) |
| | | | | | | Colorless amorphous powder (32.8%) — | (KBr) 2920, 2852, 1576, 1470, 1436, 1404, 1348, 1286, 1266, 1232, 1134, 1088, 1048, 760, 740. | 1.35–2.40(6H, m), 2.55–3.41(2H, m), 3.86–4.05(2H, m), 4.15–4.36(2H, m), 4.69(2H, s), 4.96–5.21(1H, m), 6.70 (1H, d, J=6Hz), 6.93–7.76(7H, m), 8.23(1H, d, J=6Hz), 8.49(1H, d, J=4Hz) |

TABLE 4-continued

[Structure: bicyclic compound with cycloheptane fused to pyridine ring bearing R and R¹ substituents, connected via S to imidazole bearing R² and R³ substituents, with A position]

| Example No. | R | R¹ | R² | R³ | A | Melting point (yield) | IR νcm⁻¹ | NMR(CDCl₃)δ |
|---|---|---|---|---|---|---|---|---|
| 43 | H | ![O(CH₂)₂N-pyrrolidinone] | H | H | CH | Colorless amorphous powder (36.5%) | (KBr) 2932, 1676, 1580, 1460, 1438, 1290, 1268, 1232, 1092, 908, 732, 648. | 1.10–3.21(12H, m), 3.50(2H, t, J=7Hz), 3.70 (2H, t, J=6Hz), 3.98–4.23(2H, m), 5.01–5.24 (1H, m), 6.66(1H, d, J=7Hz), 7.00–7.30 (2H, m), 7.30–7.75(2H, m), 8.23(1H, d, J=7Hz) |
| 44 | 3-CH₃ | 4-OCH₂CF₂CF₂H | 5-F | H | CH | Palely yellow amorphous powder (55.8%) | (KBr) 3064, 2932, 2856, 1490, 1440, 1406, 1346, 1288, 1262, 1226, 1200, 1134, 1108, 1062, 958, 836, 804. | 1.20–2.60(8H, m), 2.27(3H, s), 2.67–3.25 (2H, m), 4.14(2H, t, J=14Hz), 5.00–5.20 (1H, m), 5.35–7.50(5H, m), 8.19(1H, s) |
| 45 | 3-CH₃ | 4-OCH₃ | 5-OCH₃ | H | CH | Yellow amorphous powder (36.8%) | (KBr) 2924, 2848, 1468, 1450, 1432, 1394, 1342, 1260, 1232, 1198, 1152, 1054, 1030, 1006. | 1.40–2.46(6H, m), 2.23(3H, s), 2.65–3.35 (2H, m), 3.69(3H, s), 3.79(3H, s), 4.93–5.13(1H, m), 6.63–7.65(2H, m), 8.14(1H, s) |
| 46 | H | OCH₂CH₂OCH₃ | 5-CH₃ | H | CH | Palely yellow amorphous powder (37.6%) | (neat) 2980, 2924, 2856, 1736, 1580, 1448, 1372, 1334, 1274, 1240, 1198, 1132, 1090, 1060, 806, 754, 600. | 1.65–2.43(6H, m), 2.40(3H, s), 2.63–3.25 (2H, m), 3.46(3H, s), 3.63–3.83(2H, m), 3.99–4.24(2H, m), 4.96–5.16(1H, m), 6.68 (1H, d, J=7Hz), 6.91(1H, d, J=11Hz), 7.07–7.47(2H, m), 8.22(1H, d, J=7Hz) |
| 47 | 3-CH₃ | 4-OCH₂CF₂CF₂H | 5-OCH₃ | H | CH | Yellow amorphous powder (58.1%) | (KBr) 2928, 1452, 1400, 1344, 1270, 1226, 1198, 1154, 1100, 1062, 1026, 834, 806, 754. | 1.40–2.38(6H, m), 2.26(3H, s), 2.86–3.15 (2H, m), 3.80(3H, s), 4.12(2H, t, J=12Hz), 5.00–5.20(1H, m), 5.10, 6.03, 6.62(1H, 1×3, J=4Hz), 6.75–7.35(3H, m), 8.18(1H, s) |
| 48 | H | OCH₂CH₂OCH₃ | H | COOCH₂CH₂OCH₃ | CH | Colorless needle crystal (79.0%) 130–131° C. | (KBr) 2928, 1744, 1574, 1452, 1382, 1324, 1300, 1282, 1264, 1192, 1120, 1078, 758. | 1.20–2.97(8H, m), 3.44(6H, s), 3.63–3.91 (4H, m), 4.03–4.23(2H, m), 4.50–4.73(2H, m), 5.68(1H, d, J=7Hz), 6.66(1H, d, J=6Hz), 7.07–7.33(2H, m), 7.46–7.70(1H, m), 7.76–7.96 (1H, m), 8.21(1H, d, J=6Hz) |
| 49 | 3-CH₃ | OCH₂CH₂OCH₃ | H | H | CH | Colorless amorphous powder (43.9%) | (KBr) 2920, 1440, 1401, 1269, 1058, 748. | 1.30–1.65(7H, m), 3.49(3H, s), 2.93–3.60 (1H, m), 3.86(3H, s), 3.95–4.15(2H, m, J=7 Hz), 4.20–4.40(2H, d, J=7Hz), 5.52–6.70 (1H, m), 7.70–8.43(4H, m), 8.95(1H, s) |
| 50 | 3-CH₃ | OCH₂CH₂OCH₃ | 5-F | H | CH | Colorless amorphous powder (31.3%) | (KBr) 2920, 1438, 1401, 1340, 1259, 1129, 1051, 959. | 1.50–2.35(7H, m), 3.86(3H, s), 2.70–3.22 (1H, m), 3.42(3H, s), 3.55–3.80(2H, d, J=6 Hz), 3.80–4.00(2H, d, J=6Hz), 4.97–5.20 (1H, m), 6.69–7.52(3H, m), 8.15(1H, s) |
| 51 | 3-CH₃ | OCH₃ | 5-F | H | CH | Colorless amor- | (KBr) 2926, 2854, 1470, 1437, | 1.25–2.50(6H, m), 2.26(3H, s), 2.63–3.36 |

TABLE 4-continued

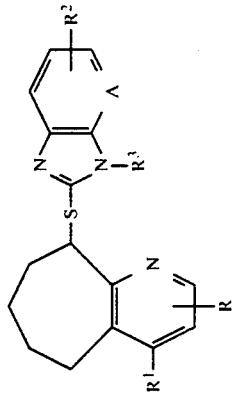

| Example No. | R | $R^1$ | $R^2$ | $R^3$ | A | Melting point (yield) | IR $\nu$cm$^{-1}$ | NMR(CDCl$_3$)$\delta$ |
|---|---|---|---|---|---|---|---|---|
| 52 | H | OCH$_3$ | H | CH$_2$COOEt | CH | phous powder (65.1%) | 1404, 1347, 1260, 1134, 750, | (2H, m), 4.72(3H, s), 5.00-5.16(1H, m), 6.74-7.50(3H, m), 8.15(1H, s) |
| 53 | 3-CH$_3$ | OCH$_3$ | H | H | CH | Colorless powder (66.8%) 162-163.5° C. | (KBr) 2976, 2924, 1736, 1578, 1474, 1460, 1440, 1330, 1310, 1282, 1244, 1210, 1054, 1024, | 1.23(3H, t, J = 9Hz), 1.56-2.76(7H, m), 3.10-3.48(1H, m), 3.82(3H, s), 4.17(2H, q J = 9Hz), 4.92(2H, s), 5.62(1H, d, J = 12Hz), 6.66(1H, d, J = 7.5Hz), 7.07-7.83(4H, m), 8.22(1H, d, J = 7.5Hz) |
| 54 | H | OCH$_3$ | 5-CH$_3$ | H | CH | Colorless powder (57.4%) 196-196.5° C. | (KBr) 3432, 2928, 2856, 1468, 1440, 1398, 1270, | 1.30-2.42(7H, m), 2.23(3H, s), 2.73-3.15 (1H, m), 3.70(3H, s), 5.01-5.16(1H, m) 6.96-7.71(4H, m), 8.15(1H, s) |
| 55 | 3-CH$_3$ | SCH$_2$CH$_2$CH$_3$ | H | H | CH | Colorless amorphous powder (74.0%) 94-95° C. | (KBr) 2920, 2848, 1578, 1470, 1437, 1275, 1230, 1050, 801, | 1.39-3.40(8H, m), 1.42(3H, s), 3.83(3H, s), 5.00-5.17(1H, t, J = 5Hz), 6.63-6.77(1H, d, J = 7Hz), 6.86-7.03(1H, d, J = 10Hz), 7.10-7.53 (2H, m), 8.03-8.18(1H, d, J = 6Hz) |
| 56 | H | OCH$_2$CH$_2$OCH$_3$ | H | H | CH | Colorless amorphous powder (62.4%) 182-183° C. | (KBr) 2962, 2920, 2848, 1440, 1401, 1377, 1350, 1269, 1236, 744, | 0.87-1.13(3H, t, J = 7Hz), 1.12-2.40(8H, m), 2.49(3H, s), 2.50-2.76(2H, t, J = 7Hz), 3.00-3.79(2H, m), 5.06-5.28(1H, m), 7.00-7.27 (2H, m), 7.35-7.60(1H, m), 8.21(1H, s), |
| 57 | H | OCH$_3$ | H | H | N | Colorless amorphous powder (26.3%) | (KBr) 2921, 1578, 1450, 1396, 1269, 1232, 1122, 1057, | 1.44-3.22(8H, m), 3.41(3H, s), 3.63-3.85 (2H, m), 4.00-4.22(2H, m), 5.08-5.25(1H, m), 6.65-6.77(1H, d, J = 7Hz), 6.96-7.18(1H, m), 7.68-8.89(1H, m), 8.10-8.38(2H, m) |
| 58 | 3-CH$_3$ | H | H | H | N | Colorless powder (25.8%) | (KBr) 2950, 1590, 1468, 1408, 1293, 1065, 759, | 1.30-3.16(8H, m), 3.83(3H, s), 5.09-5.28 (1H, m), 6.60-6.77(1H, m), 6.96-7.18(1H, m), 7.56-7.86(1H, m), 8.08-8.37(2H, m). |
| 59 | 3-CH$_3$ | OCH$_3$ | H | H | N | Colorless powder (21.0%) | (KBr) 2930, 1470, 1401, 1060, 799, | 1.44-3.30(8H, m), 2.28(3H, s), 5.10-5.31 (1H, m), 6.92-7.35(2H, m), 7.70-7.93 (1H, d, J = 10Hz), 8.05-8.38(2H, s) |
| 60 | 3-CH$_3$ | OCH$_2$CF$_2$CF$_2$H | H | H | N | Colorless powder (46.1%) | (KBr) 2930, 1590, 1470, 1070, 810, | 1.30-3.42(8H, m), 2.24(3H, s), 3.72(3H, s), 5.06-5.20(1H, m), 6.98-7.20(1H, m), 7.69-7.86(1H, d, J = 10Hz), 8.20(2H, s) |
|  | 3-CH$_3$ |  |  |  | N | Colorless amorphous powder (53.5%) | (KBr) 2925, 1456, 1397, 1272, 1011, 957, 779, | 1.60-2.30(5H, m), 2.26(3H, s), 2.87-3.21 (3H, m), 3.95-4.32(3H, t, J = 12Hz), 5.17-5.39 (1H, m), 5.38-6.71(2H, m), 6.96-7.23(1H, m), 7.72-7.91(1H, d, J = 9Hz), 8.15-8.31(2H, s) |

EXAMPLE 61

9-(5-Methoxybenzimidazole-2-yl)sulfinyl-4-methoxy-2,3-cycloheptenopyridine 940 mg (2.64 mmol) of 9-(5-methoxybenzimidazole-2-yl)thio-4-methoxy-2,3-cycloheptenopyridine is dissolved in 48 ml of dry methylene chloride, 456 mg (2.64 mmol) of m-chloroperbenzoic acid is added portionwise with stirring at −18° C., and the mixture is stirred for 20 minutes. After the reaction, a saturated aqueous sodium hydrogen carbonate solution is added, followed by extraction with methylene chloride. The methylene chloride layer is washed with saturated saline and dried over anhydrous magnesium sulfate, and the solvent is distilled away under reduced pressure. The resulting crystalline residue is recrystallized from chloroform-ether to obtain 564 mg (57.4%) of 9-(5-methoxybenzimidazole-2-yl)sulfinyl-4-methoxy-2,3-cycloheptenopyridine as yellowish powder having a melting point of 145° to 148° C.

IR$\nu$ max(KBr): 2936, 1580, 1476, 1436, 1286, 1008 cm$^{-1}$.

NMR(CDCl$_3$)$\delta$: 0.98-2.43(7H,m), 2.83-3.33 (1H,m), 3.78(6H,s), 4.79-5.05 (1H,m), 6.68(1H,d,J=6 Hz), 6.84(1H,d,J=8 Hz), 7.00-7.87 (2H,m), 8.30(1H,d,J=6 Hz).

EXAMPLE 62

4-Ethoxy-9-(5-methoxybenzimidazole-2-yl)sulfinyl-3-methyl-2,3-cycloheptenopyridine In a stream of argon, 794 mg (2.07 mmol) of 4-ethoxy-9-(5-methoxybenzimidazole-2-yl)thio-3-methyl-2,3-cycloheptenopyridine is dissolved in 25 ml of methylene chloride, 424 mg (1.97 mmol) of m-chloroperbenzoic acid dissolved in 13 ml of methylene chloride is added dropwise thereto with stirring at −12° C., and the mixture is stirred at the temperature for 5 minutes. After completion of the reaction, the reaction mixture is poured into a saturated sodium hydrogen carbonate solution, followed by extraction with methylene chloride. The methylene chloride layer is washed with water and saturated saline and dried over anhydrous magnesium sulfate, and the solvent is distilled away under reduced pressure. The resulting residue is crystallized from methylene chloride-ether to obtain 427 mg (51.6%) of 4-ethoxy-9-(5-methoxybenzimidazole-2-yl)sulfinyl-3-methyl-2,3-cycloheptenopyridine as pale yellow powder having a melting point of 152° to 154° C.

IR$\nu$ max(KBr): 2976, 2932, 1626, 1462, 1442, 1404, 1204, 1184, 1154, 1054, 1024, 998, 962, 818, 808 cm$^{-1}$.

NMR(CDCl$_3$)$\delta$: 1.00-2.65(8H,m), 1.31(3H,t,J =7 Hz), 2.19(3H,s), 2.73-3.66 (2H,m), 3.82(3H,s), 4.86-5.23 (1H,m), 6.55(1H,bs), 6.85(1H, bd,J=9 Hz), 7.62(1H,bd,J=9 Hz), 8.20(1H,bs).

EXAMPLE 63

9-[1-(Benzyloxycarbonyl)benzimidazole-2-yl]sulfinyl-4-methoxy-2,3-cycloheptenopyridine In a stream of argon, 630 mg (1.37 mmol) of 9-[1-(benzyloxycarbonyl)benzimidazole-2-yl]thio-4-methoxy-2,3-cycloheptenopyridine is dissolved in 20 ml of methylene chloride, and under stirring at −20° C. to −10° C., 281 mg (1.30 mmol) of m-chloroperbenzoic acid dissolved in 10 ml of methylene chloride is dropwise added little by little. After stirring at −10° C. to 0° C. for 50 minutes, the reaction mixture is poured into a saturated aqueous sodium hydrogen carbonate solution, followed by extraction with methylene chloride. The methylene chloride layer is washed with water and saturated saline ad dried over anhydrous magnesium sulfate, and the solvent is distilled away under reduced pressure. The residue is crystallized from methylene chloride-ether-hexane and further recrystallized from methylene chloride-ether to obtain 171 mg (27.9%) of 9-[1-(benzyloxycarbonyl)benzimidazole-2-yl]sulfinyl-4-methoxy-2,3-cycloheptenopyridine as colorless powder having a melting point of 91° to 95° C.

IR$\nu$ max(KBr): 2928, 2852, 1752, 1734, 1580, 1474, 1440, 1396, 1332, 1304, 1284, 1256, 1204, 1118, 1074 cm$^{-1}$.

NMR(CDCl$_3$)$\delta$: 1.62-2.67(7H,m), 3.06-3.45 (1H,m), 3.77(3H,s), 4.85(1H,d,J =10.5 Hz), 5.43(2H,s), 6.55 (1H,d,J=7.5 Hz), 7.06-7.53(6H,m), 7.56-8.06(2H,m), 7.99(1H,d,J=7.5 Hz).

EXAMPLE 64

9-[1-(t-Butoxycarbonylmethoxymethyl)benzimidazole-2 2-yl]sulfinyl-4-methoxy-2,3-cycloheptenopyridine In a stream of argon, 469 mg (1.00 mmol) of 9-[1-(t butoxycarbonylmethoxymethyl)benzimidazole-2-yl]-thio-4-methoxy-2,3-cycloheptenopyridine is dissolved in 20 ml of methylene chloride, 205 mg (0.95 mmol) of m-chloroperbenzoic acid dissolved in 10 ml of methylene chlordie is added dropwise little by little under stirring at −20° C. to −10° C., and the mixture is stirred at that temperature for 1 hour. The reaction mixture is poured into a saturated aqueous sodium hydrogen carbonate solution, followed by extraction with methylene chloride. The methylene chloride layer is washed with water and saturated saline and dried over anhydrous magnesium sulfate, and the solvent is distilled away under reduced pressure. The residue is purified by activated alumina column chromatography (ethyl acetate-hexane 1:2→1:1 →ethyl acetate) to obtain 165 mg (35.2%) of 9-[1-(t-butoxycarbonylmethoxymethyl)benzimidazole-2-yl]sulfinyl-4-methoxy-2,3-cycloheptenopyridine.

IR$\nu$ max(KBr): 2976, 2932, 1742, 1580, 1474, 1450, 1368, 1284, 1238, 1156, 1054 cm$^{-1}$.

NMR(CDCl$_3$)$\delta$: 1.45(9H,s), 1.63-2.76(7H,m), 3.06-3.42(1H,m), 3.81(3H,s), 4.97(1H,dJ=9.0 Hz), 5.13(2H,s), 5.67(1H,d,J=13.5 Hz), 5.91(1H,d,J =13.5 Hz), 6.65(1H,d,J=7.5 Hz), 7.04-7.90(4H,m), 8.22(1H,d,J=7.5 Hz).

EXAMPLE 65

9-[1-(Ethoxycarbonyl)benzimidazole-2-yl]sulfinyl-4-methoxy-2,3-cycloheptenopyridine In a stream of argon, 227 mg (0.62 mmol) of 9-(benzimidazole-2-yl)sulfinyl-4-methoxy-2,3-cycloheptenopyridine sodium salt is dissolved in 15 ml of dry THF, 0.09 ml (0.93 mmol) of ethyl chlorocarbonate is added dropwise under stirring at room temperature, and the mixture is stirred for 1 hour. After the reaction, the solvent is distilled away under reduced pressure, the residue is dissolved in methylene chloride, and the solution is washed with water. The methylene chloride layer is dried over anhydrous magnesium sulfate, the solvent is distilled away under reduced pressure, and the solid residue is recrystallized from methylene chloride-ether to obtain 194 mg (75.2%) of 9[(1-ethoxycarbonyl)benzimidazole-2-yl]sulfinyl-4-methoxy-2,3-cycloheptenopyridine as colorless powder having a melting point of 183° to 185° C.

IRν max(KBr): 2924, 1756, 1578, 1472, 1450, 1428, 1400, 1376, 1342, 1316, 1296, 1282, 1260, 1186, 1020, 756, 738 cm⁻¹.

NMR(CDCl₃)δ: 1.08-2.73(7H,m), 1.43(3H,t,J=7 Hz), 3.13-3.50(1H,m), 3.78 (3H,s), 4.53(2H,q,J=7 Hz), 4.93 (1H,d,J=9 Hz), 6.58(1H,d,J=5 Hz), 7.20-7.53(2H,m), 7.81-8.02 (2H,m), 8.08(1H,d,J=5 Hz).

EXAMPLE 66

9-(Benzimidazole-2-yl)sulfinyl-4-methoxy-2,3-cycloheptenopyridine sodium salt

In a stream of argon, 100g (527 mmol) of 28% sodium methylate and 530 ml of dry methylene chloride are placed in a 5 l three-necked flask, and under stirring at room temperature, 120 g (350 mmol) of 9-(benzimidazole-2-yl)sulfinyl-4-methoxy-2,3-cycloheptenopyridine is added, and the mixture is stirred for 2 hours.

Then, ether is added dropwise, and after 30 minutes stirring at room tempeature, the mixture is stirred at −30° C. for 2 hours. The deposited crystals are collected by filtration, and after removal of the methanol insoluble matters and acetone insoluble matters, recrystallized from methylene chloride-ether to obtain 107 g (83.9%) of 9-(benzimidazole-2-yl)sulfinyl-4-methoxy-2,3-cycloheptenopyridine sodium salt as colorless powder having a melting point of 167° to 175° C. (decomposition).

IRν max(KBr): 3372, 3048, 2972, 2928, 2856, 1580, 1474, 1298, 1270, 1090, 1052, 1036, 820, 800, 744 cm⁻¹.

NMR(CDCl₃-DMSO-d₆)δ: 1.00-2.63(7H,m), 2.95-3.34(1H,m), 3.82(3H,s), 4.75(1H,d,J=6 Hz), 6.65(1H,d,J=5 Hz), 6.85-7.10(2H,m), 7.40-7.65 (2H,m), 8.23(1H,d,J=5 Hz).

EXAMPLE 67

9-(Benzimidazole-2-yl)sulfinyl-4-methoxy-2,3-cycloheptenopyridine potassium salt In a stream of argon, 342 mg (1.00 mmol) of 9-(benzimidazole-2-yl)sulfinyl-4-methoxy-2,3-cyclheptenopyridine is dissolved in 5 ml of dry methylene chloride, 137 mg (1.20 mmol) of potassium t-butoxide is added, and the mixture is stirred at room temperature for 16.5 hours.

Then, ether is added dropwise, followed by stirring at room temperature for 2 hours. The deposited crystals are collected by filtration, and recrystallized from chloroform and then from methanol-ether to obtain 110 mg (28.9%) of 9-(benzimidazole-2-yl)sulfinyl-4-methoxy-2,3-cycloheptenopyridine potassium salt as colorless powder having a melting point of 159° to 163° C. (decomposition).

IRν max(KBr): 3400, 2924, 1580, 1476, 1460, 1428, 1376, 1308, 1288, 1264, 1082, 1058, 1030, 802, 742 cm⁻¹.

NMR(CDCl₃-DMSO-d₆)δ: 1.00-2.73(7H,m), 3.00-3.45(1H,m), 3.79(3H,s), 4.81(1H,bs), 6.52(1H,d,J=5 Hz), 6.77-7.06(2H,m), 7.32-7.63(2H,m), (2H,m), 8.13(1H,d,J=5 Hz).

EXAMPLE 68

9-[pyrido[2,3-d]imidazole-2-yl]sulfinyl-2,3-cycloheptenopyridine

In a stream of argon, 700 g (2.36 mmol) of 9-[pyriod[2,3-d]imidazole-2-yl]thio-2,3-cyclheptenopyridine is dissolved in 25 ml of methylene chloride, 358 mg (2.25 mmol) of m-chloroperbenzoic acid dissolved in 4 ml of methylene chloride is added dropwise with stirring at −18° C., and the mixture is stirred at the same temperature for 5 minutes. After completion of the reaction, the reaction mixture is poured into a saturated aqueous sodium hydrogen carbonate solution and extracted with methylene chloride. The methylene chloride layer is washed with water and saturated saline and dried over anhydrous magnesium sulfate, and the solvent is distilled away under reduced pressure. The resulting residue is crystallized from methylene chloride-ether to obtain 252 mg (34.2%) of 9-[pyrido[2,3-d]imidazole-2-yl]sulfinyl-2,3-cycloheptenopyridine as colorless crystals having a melting point of 133.5° to 135° C.

IR0max(KBr): 2960, 1635, 1455, 1295, 1064, 821 cm⁻¹.

NMR(CDCl₃): 1.10-2.28(5H,m), 2.28-3.20 (3H,m), 4.56-4.86(1H,m), 6.83-7.60(3H,m), 7.90-8.40(2H,m), 8.70-8.40(1H,m).

The compounds shown in Table-5 are obtained in the same manner as in Examples 61 to 68.

TABLE 5

[Structure: bicyclic compound with cycloheptane fused to pyridine (bearing R¹ and R), linked via S(=O) to an imidazole (bearing R³ on N) fused to a pyridine ring (A position, bearing R²)]

| Example No. | R | R¹ | R² | R³ | A | Melting point (yield) | IR νcm⁻¹ | NMR(CDCl₃)δ |
|---|---|---|---|---|---|---|---|---|
| 69 | H | H | 5-OCH₃ | H | CH | Colorless powder (55.7%) 132-134° C. | (KBr) 3116, 3092, 2940, 1626, 1454, 1438 1198, 1026, 820, | 1.15-2.33(6H, m), 2.53-2.84(2H, m), 3.79 (3H, s), 4.84-5.08(1H, m), 6.47 7.78 (5H, m), 8.35(1H, d, J=5Hz) |
| 70 | H | H | 5-NO₂ | H | CH | Yellow powder (48.8%) 129-134° C. | (KBr) 2935, 2858, 1620, 1522, 1434, 1342, 1040, 812, 738, | 0.73-3.18(8H, m), 4.73-5.18(1H, m), 6.94-7.73(3H, m), 7.96-8.57(3H, m) |
| 71 | H | H | 5-Cl | H | CH | Yellowish amorphous powder (40.0%) — | (KBr) 3072, 2932, 2852, 1615, 1578, 1454, 1434, 1042, 920, 806, | 1.03-2.46(6H, m), 2.62-2.93(2H, m), 4.70-5.04(1H, m), 6.86-7.87(5H, m), 8.31(1H, d, J=5Hz) |
| 72 | H | H | 5-F | H | CH | Colorless powder (33.0%) 155-156° C. | (KBr) 3064, 2858, 1626, 1578, 1490, 1454, 1434, 1348, 1108, 1028, 968, 802, 748, | 1.13-2.40(6H, m), 2.45-3.09(2H, m), 4.85-5.13(1H, m), 6.68-7.90(5H, m), 8.35(1H, d, J=6Hz) |
| 73 | H | H | 5-CH₃ | H | CH | Yellowish amorphous powder (64.8%) — | (KBr) 3056, 2982, 2856, 1578, 1454, 1434, 1038, 968, 804, 754. | 1.23-2.15(6H, m), 2.40(3H, s), 2.43-2.96 (2H, m), 4.83-5.18(1H, m), 6.78-7.83 (5H, m), 8.34(1H, d, J=5Hz) |
| 74 | H | H | 5-CF₃ | H | CH | Palely yellow amorphous powser (34.4%) — | (KBr) 2932, 2856, 1434, 1330, 1162, 1120, 1048, 814, | 1.13-2.35(6H, m), 2.46-3.03(2H, m), 4.83-5.21(1H, m), 6.90-8.10(5H, m), 8.27(1H, d, J=5Hz) |
| 75 | H | OCH₃ | H | H | CH | Yellowish powder (63.5%) 147-150° C. | (KBr) 3068, 2972, 2932, 2852, 1580, 1476, 1454, 1430, 1286, 1270, 1086, 1054, 996, 746, | 1.07-2.74(6H, m), 2.95-3.40(2H, m), 3.82 (3H, s), 4.73-4.98(1H, m), 6.69(1H, d, J=6 Hz), 7.06-7.92(4H, m), 8.30(1H, d, J=6Hz) |
| 76 | H | OCH₃ | 5-F | H | CH | Colorless powder (46.3%) 161-163° C. | (KBr) 3068, 2976, 2940, 2856, 1620, 1580, 1476, 1430, 1284, 1276, 1088, 1058, 994, 812, | 1.00-2.55(6H, m), 2.92-3.30(2H, m), 3.79 (3H, s), 4.73-5.05(1H, m), 6.68(1H, d, J 5 Hz), 6.77-7.76(3H, m), 8.28(1H, d, J=5Hz) |
| 77 | H | OEt | H | H | CH | Palely brown powder (52.4%) 112-118° C. | (KBr) 3430, 3064, 2976, 2928, 1580, 1466, 1430, 1312, 1286, 1268, 1052, 744, | 1.43(3H, t, J=7.5Hz), 1.60-2.65(7H, m), 3.03-3.36(1H, m), 4.03(2H, q, J 7.5Hz), 4.93(1H, d, J=6Hz), 6.65(1H, d, J 7.5Hz), 7.09-7.70(4H, m), 8.26(1H, d, J 7.5Hz) |
| 78 | H | Oⁿ-Bu | H | H | CH | Colorless needle crystal (58.0%) 150-154° C. (decomposed) | (KBr) 3450, 3056, 2960, 2936, 1588, 1466, 1428, 1310, 1290, 1268, 1046, | 0.96(3H, t, J=7.5Hz), 1.13-2.56(11H, m), 3.05-3.34(1H, m), 3.95(2H, t, J=7.5Hz), 4.80(1H, d, J=9Hz), 6.67(1H, d, J 7.5Hz), 7.10-7.93(4H, m), 8.26(1H, d, 7.5Hz) |

TABLE 5-continued

[Structure shown at top of table: a cyclohepta-fused imidazo[pyridine] with S(=O) linker to a pyridine bearing R and R², N-R³, and R¹ substituent]

| Example No. | R | R¹ | R² | R³ | A | Melting point (yield) | IR ν cm⁻¹ | NMR(CDCl₃)δ |
|---|---|---|---|---|---|---|---|---|
| 79 | H | 4-methylphenyl (p-tolyl) | H | H | CH | Colorless prismatic crystal (66.2%) 162–165° C. | (KBr) 3500, 3040, 2936, 2856, 1576, 1506, 1466, 1428, 1268, 1242, 1206, 1008. | 1.12–2.70(7H, m), 2.33(3H, s), 3.10–3.53 (1H, m), 4.89(1H, d, J=7.5Hz), 6.50(1H, d, J=7.5Hz), 6.76(2H, d, J=10.5Hz), 6.96–7.93(4H, m), 7.16(2H, 6(2H, d, J=10.5Hz), 8.20(1H, d, J=10.5Hz). |
| 80 | H | cyclopropylmethoxy | H | H | CH | Palely brown prismatic crystal (59.8%) 138–140° C. (decomposed) | (KBr) 3456, 3012, 2944, 2872, 2808, 1580, 1472, 1452, 1428, 1412, 1298, 1266, 1038, 1008, | 0.20–0.76(4H, m), 1.05–2.66(8H, m), 3.10–3.52(1H, m), 3.12(2H, d, J=7.5Hz), 4.75 (1H, d, J=10.5Hz), 6.65(1H, d, J=7.5Hz), 7.06–7.95(4H, m), 8.25(1H, d, J=7.5Hz) |
| 81 | H | (tetrahydrofuran-2-yl)methoxy | H | H | CH | Colorless powder (55.2%) 147–148° C. (decomposed) | (KBr) 3432, 3068, 2972, 2932, 1578, 1464, 1432, 1290, 1268, 1052, 1006, | 1.13–2.63(7H, m), 3.10–3.48(1H, m), 3.68–4.43(5H, m), 4.75(1H, d, J=10.5Hz), 6.73(1H, d, J=7.5Hz), 8.20(1H, d, J=7.5Hz) |
| 82 | H | OCH₃ | H | CH₂OCOCH₃ | CH | Colorless powder (10.5%) 141–144° C. | (KBr) 2932, 1752, 1580, 1466, 1440, 1364, 1350, 1284, 1252, 1206, 1088, 1050, 1024, | 1.23–2.81(7H, m), 2.10(3H, s), 3.06–3.46 (1H, m), 3.81(3H, s), 5.11(1H, d, J=9Hz), 6.46, 6.76(1H×2, d, J=13.5Hz), 6.63(1H, d, J=7.5Hz), 7.10–7.93(4H, m), 8.15(1H, d, J=7.5Hz). |
| 83 | H | OCH₃ | H | CH₂OCH₃ | CH | Colorless powder (25.9%) 132–136° C. | (KBr) 2920, 1580, 1476, 1434, 1334, 1318, 1286, 1262, 1110, 1092, 1044, | 1.23–2.80(7H, m), 3.10–3.53(1H, m), 3.41(3H, s), 3.82(3H, s), 5.02–5.29 (1H, m), 5.75, 6.06(1H×2, d, J=13.5Hz), 6.65(1H, d, J=7.5Hz), 7.13–7.93(4H, m), 8.16(1H, d, J=7.5Hz) |
| 84 | H | OCH₃ | H | CH₂OEt | CH | Colorless powder (51.8%) 112–114° C. | (KBr) 2928, 2852, 1580, 1474, 1438, 1340, 1092, 1052, | 1.19(3H, t, J=9Hz), 1.48–2.83(7H, m), 3.08–3.43(1H, m), 3.62(2H, q, J=9Hz), 3.08(3H, s), 5.03–5.33(1H, m), 5.76, 5.98 (1H×2, d, J=13.5Hz), 6.65(1H, d, J=7.5Hz), 7.14–7.90(4H, m), 8.16(1H, d, J=7.5Hz) |
| 85 | H | OCH₃ | H | CH₂O(CH₂)₂OCH₃ | CH | Colorless amorphous powder (47.7%) 45–49° C. | (KBr) 2924, 2852, 1588, 1464, 1438, 1336, 1316, 1284, 1134, 1090, | 1.34–2.80(8H, m), 3.30(3H, s), 3.47(2H, t, J=6Hz), 3.73(2H, t, J=6Hz), 3.80(3H, s), 5.12(1H, d, J=9Hz), 5.84, 6.13(1H×2, d, J=13.5Hz), 6.65(1H, d, J=7.5Hz), 7.13–7.92(4H, m), 8.13(1H, d, J=7.5Hz) |

TABLE 5-continued

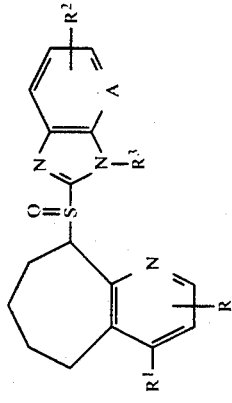

| Example No. | R | R¹ | R² | R³ | A | Melting point (yield) | IR νcm⁻¹ | NMR(CDCl₃)δ |
|---|---|---|---|---|---|---|---|---|
| 86 | H | OCH₃ | H | COO(CH₂)₂OCH₃ | CH | Colorless powder (35.7%) 176-179° C. | (KBr) 2920, 1746, 1580, 1474, 1448, 1380, 1330, 1284, 1256, 1206, 1078, | 1.53-2.75(8H, m), 3.33(3H, s), 3.66(2H, t, J=6Hz), 3.76(3H, s), 4.57(2H, t, J=6Hz), 4.89(1H, d, J=12Hz), 6.56(1H, d, J=7.5Hz), 7.08-8.15(4H, m), 8.09(1H, d, J=7.5Hz) |
| 87 | H | OCH₃ | H | CH₂COOEt | CH | Colorless powder (24.2%) | (KBr) 2932, 2852, 1744, 1580, 1476, 1448, 1308, 1222, 1048, | 1.26(3H, t, J=9Hz), 1.60-2.76(7H, m), 3.06-3.37(1H, m), 3.81(3H, s), 4.23(2H, q, J=9Hz), 4.94-5.17(1H, m), 5.13, 5.78 (1H×2, d, J=22.5Hz), 6.65(1H, d, J=7.5Hz), 7.04-7.86(4H, m), 8.20(1H, d, J=7.5Hz) |
| 88 | 3-CH₃ | OCH₃ | H | H | CH | Colorless powder (64.2%) 166-168° C. (decomposed) | (KBr) 3448, 3070, 2932, 1470, 1455, 1434, 1398, 1266, 1056, 1011. | 1.38-2.70(7H, m), 2.23(3H, s), 2.87-3.26 (1H, m), 3.55(3H, s), 4.86(1H, d, J=9Hz), 7.03-7.84(4H, m), 8.20(1H, s) |
| 89 | 3-CH₃ | OCH₃ | H | Na⁺ | CH | Colorless powder (67.7%) 189-195° C. (decomposed) | (KBr) 3432, 2932, 1562, 1470, 1450, 1380, 1290, 1270, 1056, 1006. | *1 |
| 90 | H | OCH₂CH₂OCH₃ | F | H | CH | Colorless powder (51.7%) 141-143° C. | (KBr) 3036, 2988, 2936, 2880, 2788, 1576, 1476, 1448, 1430, 1406, 1276, 1132, 1106, 1086, 1064, 1036, 1016, 994, 966, 836, 806, 796, | 1.33-2.26(7H, m), 2.10(3H, s), 2.84-3.25 (1H, m), 3.63(3H, s), 4.60-4.85(1H, m), 6.76-7.10(2H, m), 7.30-7.63(2H, m), 8.02(1H, s) |
| 91 | H | OCH₃ | 5,6-OCH₃ | H | CH | Colorless powder (71.8%) 176-178° C. (decomposed) | (KBr) 3064, 2976, 2932, 2856, 1580, 1490, 1478, 1434, 1326, 1284, 1240, 1194, 1180, 1140, 1054, 1008, 998, 830, | 1.00-2.65(7H, m), 2.97-3.30(1H, m), 3.39 (3H, s), 3.58-3.81(2H, m), 3.93-4.21(3H, m), 4.70-5.01(1H, m), 6.69(1H, d, J=6Hz), 6.70-7.80(3H, m), 8.24(1H, d, J=6Hz) |
| 92 | H | OCH₂CF₃ | H | H | CH | Colorless powder (39.2%) | (KBr) 3412, 3304, 2932, 1580, 1292, 1454, 1436, 1370, 1318, 1294, 1266, 1160, 1142, 1102, 1044, 976, | 1.00-3.30(8H, m), 3.80(3H, s), 3.87(6H, s), 4.85-5.12(1H, m), 6.65-6.80(2H, d, J=6Hz), 7.06-7.30(1H, m), 8.29(1H, d, J=6Hz) *2 |
| 93 | H | OCH₂CH=CH₂ | H | H | CH | Yellow amorphous powder (37.7%) | (KBr) 2952, 2920, 2872, 1580, 1472, 1426, 1310, 1298, 1282, 1040, 1014, 994, 750, 746, | 1.36-3.40(8H, m), 4.47(2H, m), 4.73-4.95 (1H, m), 6.77(1H, d, J=6Hz), 7.16-7.37 (2H, m), 7.53-7.81(2H, m), 8.44(1H, d, J=6Hz) |
| 94 | H | OCH₂CH₂OCH₃ | H | H | CH | Colorless powder | (KBr) 2924, 2876, 2852, 1580, | 1.00-3.33(8H, m), 4.35-4.63(2H, m), 4.67-5.00(1H, m), 5.07-5.56(2H, m), 5.70-6.20(1H, m), 6.57(1H, d, J=7Hz), 6.92-7.33(2H, m), 7.36-8.07(3H, m), 8.18(1H, d, J=7Hz) 1.00-2.70(8H, m), 3.39(3H, s), 3.60-1.82 |

TABLE 5-continued

[Structure shown: bicyclic system with N, S(=O), with substituents R, R¹, R², R³, and A]

| Example No. | R | R² | R¹ | R³ | A | Melting point (yield) | IR ν cm⁻¹ | NMR(CDCl₃)δ |
|---|---|---|---|---|---|---|---|---|
| 95 | H | H | OCH₂CH₂OH | H | CH | (42.0%) | 1472, 1452, 1428, 1270, 1082, 1052, 998, 750. | (2H, m), 3.95–4.21(2H, m), 4.78–5.03 (1H, m), 6.66(1H, d, J=6Hz), 7.07–7.34 (2H, m), 7.36–7.67(2H, m), 8.24(1H, d, J=6Hz) |
| 96 | H | H | OCH₂CH₂OCOCH₃ (with C=O) | H | CH | Yellow amorphous powder (24.3%) | (KBr) 3416, 2928, 2856, 1580, 1472, 1450, 1312, 1290, 1270, 1240, 1136, 1078, 1054, 946, 904, 800, 746. | 1.00–3.60(8H, m), 3.80–4.33(4H, m), 4.66–5.00(1H, m), 6.68(1H, d, J=6Hz), 7.06–7.83(4H, m), 8.23(1H, d, J=6Hz) |
| 97 | H | H | O(CH₂)₃OCH₃ | H | CH | Paley orange powder (34.3%) 135–137° C. | (KBr) 3064, 2968, 2936, 2856, 1736, 1580, 1452, 1432, 1286, 1268, 1250, 1230, 1092, 1058, 1006, 744. | 1.06–3.43(8H, m), 2.08(3H, s), 4.05–4.28 (2H, m), 4.33–4.53(2H, m), 4.69–4.96 (1H, m), 4.68(1H, d, J=5Hz), 7.10–8.00 (4H, m), 8.28(1H, d, J=5Hz) |
| 98 | H | H | O(CH₂)₂OCH₂Ph | H | CH | Colorless powder (28.4%) 135–136.5° C. | (KBr) 3064, 3012, 2932, 2872, 2808, 1580, 1478, 1458, 1430, 1412, 1310, 1288, 1270, 1192, 1138, 1118, 1096, 1082, 1054, 1006, 816, 800, 750. | 0.99–2.65(10H, m), 3.31(3H, s), 3.50(2H, t, J=6Hz), 4.06(2H, t, J=6Hz), 4.63–4.93(1H, m), 6.70(1H, d, J=6Hz), 7.03–7.70(4H, m), 8.27(1H, d, J=6Hz) |
| 99 | H | H | O(CH₂)₂OPh | H | CH | Yellow amorphous powder (89.3%) | (KBr) 3060, 2924, 2856, 1578, 1470, 1452, 1428, 1310, 1286, 1268, 1128, 1088, 1036, 1002, 800, 742, 606. | 1.06–1.59(8H, m), 3.67–3.93(2H, m), 3.98–4.25(2H, m), 4.57(2H, s), 4.66–4.99(1H, m), 6.67(1H, d, J=6Hz), 7.00–7.71(9H, m), 8.25(1H, d, J=6Hz) |
| 100 | H | H | O(CH₂)₂OCH₂Py | H | CH | Colorless powder (39.7%) 144–145° C. | (KBr) 3064, 2820, 1580, 1458, 1478, 1454, 1432, 1272, 1244, 1086, 1064, 1006, 814, 800, 756, 744. | 1.00–3.35(8H, m), 4.27(3H, m), 4.66–4.92 (1H, m), 6.67(1H, d, J=6Hz), 6.78–7.71 (9H, m), 8.22(1H, d, J=6Hz) |
| 101 | H | H | Yellow amorphous powder (40.0%) | H | CH | Yellow amorphous powder (40.0%) | (KBr) 3060, 2928, 2856, 1578, 1474, 1450, 1432, 1356, 1286, 1268, 1238, 1134, 1088, 1046, 1002, 800, 746. | 1.00–3.45(8H, m), 3.77–4.03(2H, m), 4.03–4.31(2H, m), 4.69(2H, s), 4.75–5.01 (1H, m), 6.68(1H, d, J=6Hz), 7.00–7.80 (7H, m), 8.25(1H, d, J=6Hz), 8.52(1H, d, J=6Hz) |
|  | H | H | O(CH₂)N (pyrrolidinone) | H | CH | Colorless powder (53.3%) 140–141° C. | (KBr) 3064, 3020, 2932, 2864, 2800, 1692, 1580, 1458, 1426, 1288, 1086, 998, 746. | 1.00–2.70(12H, m), 2.93–3.80(4H, m), 3.85–4.33(2H, m), 4.65–5.00(1H, m), 6.66(1H, d, J=5Hz), 6.98–8.06(4H, m), 8.26(1H, d, J=5Hz) |

TABLE 5-continued

| Example No. | R | R¹ | R² | R³ | A | Melting point (yield) | IR ν cm⁻¹ | NMR(CDCl₃)δ |
|---|---|---|---|---|---|---|---|---|
| 102 | H | OCH₂CF₂CHF₂ | H | Na | CH | Colorless powder (72.7%) 169-171.5° C. | (KBr) 3388, 3052, 2932, 2860, 1580, 1472, 1454, 1378, 1292, 1270, 1248, 1202, 1122, 1020, 802, 746. | *1 1.16–3.50(8H, m), 4.16–5.00(3H, m), 6.13–6.37(1H, m), 6.60–7.10(3H, m), 7.30–7.69(2H, m), 8.23(1H, d, J=6Hz) |
| 103 | H | OCH₃ | H | CH₂OH | CH | Colorless powder (42.7%) 120-122° C. | (KBr) 3256, 3060, 2924, 2852, 1580, 1474, 1432, 1340, 1314, 1282, 1244, 1136, 1054, 814, 742. | 1.14–3.50(8H, m), 3.84(3H, s), 5.07–5.33(1H, m), 5.66(1H, d, J=12Hz), 6.17(1H, d, J=12Hz), 6.72(1H, d, J=6Hz), 7.13–7.90(4H, m), 8.06–8.40(1H, m). |
| 104 | 3-CH₃ | OCH₂CF₂CF₂H | 5-F | H | CH | Colorless powder (44.8%) 163-165° C. | (KBr) 3034, 2932, 2854, 1497, 1470, 1455, 1434, 1413, 1263, 1221, 1197, 1137, 1110, 1080, 1059, 1002, 966, 954, 843, 810. | *2 1.13–3.29(8H, m), 2.21(3H, s), 3.75–4.24 (2H, m), 4.68–5.02(1H, m), 5.36–6.76 (1H, m), 6.76–7.83(3H, m), 8.17(1H, s) |
| 105 | 3-CH₃ | OCH₃ | 5-OCH₃ | H | CH | Colorless powder (60.4%) 163-165° C. (decomposed) | (KBr) 3064, 3000, 2924, 2852, 1626, 1454, 1438, 1406, 1396, 1204, 1184, 1054, 1022, 1008, 996, 962, 820, 808. | 1.10–3.20(8H, m), 2.17(3H, s), 3.41(3H, s), 3.80(3H, s), 4.86–5.26(1H, m), 6.51(1H, bs), 6.70–7.30(2H, m), 7.46–7.71(1H, d, J=10Hz), 8.18(1H, s) |
| 106 | H | OCH₂CH₂OCH₃ | 5-CH₃ | H | CH | Palely orange powder (42.7%) 118-121° C. | (neat) 3048, 2976, 2932, 2852, 1578, 1452, 1430, 1334, 1308, 1288, 1274, 1196, 1134, 1086, 1060, 1008, 966, 802. | 1.05–3.30(8H, m), 2.44(3H, s), 3.40(3H, s), 3.55–3.85(2H, m), 3.90–4.23(2H, m), 4.60–4.96(1H, m), 6.70(1H, d, J=6Hz), 6.86–7.28(2H, m), 7.36–7.80(1H, m), 8.28(1H, d, J=6Hz) |
| 107 | 3-CH₃ | OCH₂CF₂CF₂H | 5-OCH₃ | H | CH | Colorless powder (38.8%) 166-168° C. | (KBr) 3080, 3048, 3004, 2936, 2904, 1624, 1460, 1406, 1200, 1178, 1126, 1112, 1094, 1070, 996, 964, 816. | 1.07–2.03(6H, m), 2.19(3H, s), 2.26–3.15 (2H, m), 3.40–4.02(2H, m), 3.81(3H, s), 5.03–7.30(4H, m), 7.61(1H, d, J=10Hz), 8.26(1H, s) |
| 108 | H | OCH₃ | 5-CH₃ | H | CH | Colorless powder (39.5%) 155-156° C. | (KBr) 2974, 2926, 1581, 1479, 1452, 1434, 1284, 1086, 1053, 1008, 822. | 1.20–2.70(7H, m), 2.68(3H, s), 3.21–3.69 (1H, m), 4.19(3H, s), 5.20–5.45(1H, d, J=11Hz), 7.27–7.43(1H, s), 7.62–7.90(2H, m), 8.15–8.52(1H, m), 9.06–9.18 (1H, d, J=7Hz) |
| 109 | H | OCH₂CH₂OCH₃ | H | COOCH₂CH₂OCH₃ | CH | Colorless powder (16.7%) 108-110° C. | (KBr) 2926, 1746, 1578, 1449, 1419, 1374, 1323, 1305, 1287, 1254, 1206, 1119, 1077, 996, 840, 756, 747. | 1.10–2.66(6H, m), 3.36(3H, s), 3.40(3H, s), 3.55–3.83(4H, m), 3.96–4.20(2H, m), 4.40–4.71(2H, m), 4.91(1H, d, J=10Hz), 6.58(1H, d, J=6Hz), 7.15–7.51(2H, m), 7.66–8.03(2H, m), 8.08(1H, d, J=6Hz) |
| 110 | H | OCH₃ | H | H | N | Colorless powder | (KBr) 2920, 1583, 1479, 1291, | 1.19–2.70(7H, m), 3.12–3.50(1H, m), |

TABLE 5-continued

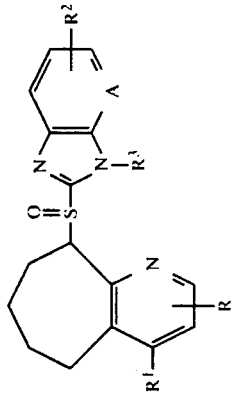

| Example No. | R | R¹ | R² | R³ | A | Melting point (yield) | IR νcm⁻¹ | NMR(CDCl₃)δ |
|---|---|---|---|---|---|---|---|---|
| 111 | H | OCH₂Ph | H | H | CH | (44.0%) 130–140° C. | 1266, 1059, 800, | 3.79(3H, s), 4.56–4.80(1H, d, J=10Hz), 6.59–6.75(1H, d, J=6Hz), 7.10–7.33(1H, dd, J=6Hz), 8.00–8.36(2H, m), 8.36–8.65 (1H, d, J=5Hz) |
| 112 | H | OCH₂CF₂CF₃ | H | H | CH | Colorless powder (62.5%) 155–158.5° C. (decomposed) | (KBr) 3064, 2932, 1578, 1474, 1462, 1454, 1432, 1284, 1268, 1044, 1024, 1010, 798, 748, 424. | 1.00–2.66(7H, m), 3.08–3.43 (1H, m), 4.84(1H, d, J=7Hz), 5.04(2H, s), 6.73(1H, d, J=5Hz), 7.10–7.93(4H, m), 7.33(5H, s), 8.27(1H, d, J=5Hz) |
| 113 | H | OCH₂CF₂CF₂H | H | H | CH | Colorless powder (60.8%) 161–162° C. (decomposed) | (KBr) 3320, 2940, 1578, 1470, 1454, 1436, 1372, 1316, 1294, 1266, 1212, 1196, 1142, 1102, 1046, 946, 748. | 1.04–2.66(7H, m), 2.95–3.40(1H, m), 4.38(2H, t, J=12Hz), 4.90(1H, d, J=6Hz), 6.63(1H, d, J=5Hz), 7.10–7.92(4H, m), 8.32(1H, d, J=5Hz) |
| 114 | H | SCH₂CH₂CH₃ | H | H | CH | Colorless powder (65.4%) 150–154° C. (decomposed) | (KBr) 3320, 2932, 1580, 1472, 1454, 1432, 1372, 1316, 1292, 1270, 1240, 1222, 1206, 1118, 1068, 1046, 946, 820, 748. | 1.15–3.52(8H, m), 4.33(2H, t, J=12Hz), 4.92(1H, d, J=6Hz), 5.28, 5.93, 6.52(1H, t×3, J=3Hz), 6.65(1H, d, J=6Hz), 7.10–7.90 ×3, J=3Hz), 8.32(1H, d, J=6Hz), 11.70(1H, br) 4H, m), 8.32(1H, d, J=6Hz), 11.70(1H, m) |
| 115 | H | ![morpholine] | H | H | CH | Colorless powder (45.2%) 133–134° C. (decomposed) | (KBr) 3068, 2960, 2928, 2868, 1564, 1452, 1432, 1406, 1266, 1024, 800, 766, 744. | 1.06(3H, t, J=7Hz), 1.25–3.67(10H, m), 2.87(2H, t, J=7Hz), 4.92(1H, d, J=6Hz), 6.96(1H, d, J=5Hz), 7.05–7.97(4H, m), 8.24(1H, d, J=5Hz) |
| 116 | H | OCH₃ | H | CH₂OCPh (C=O) | CH | Brown powder (18.4%) 143–145° C. (decomposed) | (KBr) 3456, 3064, 2932, 2856, 1630, 1578, 1452, 1430, 1266 1114, 1024, 1006, 990, 744. | *2 1.10–3.40(12H, m), 3.70–4.00(4H, m), 4.63–4.85(1H, m), 6.87(1H, d, J=6Hz), 7.18–7.80(4H, m), 8.29(1H, d, J=6Hz) |
| 117 | H | Cl | 5-OCH₃ | H | CH | Paley brown powder (23.7%) 138–141° C. | (KBr) 2912, 2848, 1734, 1578, 1282, 1254, 1088, 1064, 1048 1024, 738, 714 | 1.10–3.45(8H, m), 3.74(3H, s), 5.23–5.52 (1H, m), 6.47(1H, d, J=6Hz), 6.73, 6.91 (1H×2, d, J=11Hz), 7.86(1H, d, J=6Hz), 7.11–8.18(9H, m) |
| 118 | 3-CH₃ | OCH₂CH₂OCH₃ | H | H | CH | Colorless powder (44.2%) 153–155° C. (decomposed) | (KBr) 3224, 3080, 3004, 2936, 1626, 1560, 1504, 1454, 1406, 1304, 1204, 1176, 1150, 1030, 966, 834, 804. | 1.02–2.78(7H, m), 2.93–3.41(1H, m), 3.79 (3H, s), 5.05(1H, br), 6.56–7.75(4H, m), 8.24(1H, br) |
| | | | | | | Colorless powder (77.1%) | (KBr) 3070, 2926, 1470, 1455, 1407, 1266, 1059, 1011, 747. | 1.25–2.90(7H, m), 3.20–3.58(1H, m), 2.41 (3H, s), 3.71(3H, s), 3.96(4H, s), 5.48– |

TABLE 5-continued

| Example No. | R | R¹ | R² | R³ | A | Melting point (yield) | IRνcm⁻¹ | NMR(CDCl₃)δ |
|---|---|---|---|---|---|---|---|---|
| 119 | 3-CH₃ | OCH₂CH₂OCH₃ | 5-F | H | CH | 148-150° C. (—) | — | 5.72(1H, d, J=10Hz), 7.62-8.07(4H, m), 8.38-8.68(1H, m), 9.00(1H, s) |
| 120 | 3-CH₃ | OCH₃ | 5-F | H | CH | Colorless powder (69.5%) 146-147° C. | (KBr) 2932, 1460, 1137, 1005, 1011, 996. | 1.20-2.69(7H, m), 2.21(3H, s), 2.90-3.21 (1H, m), 3.65(3H, s), 3.45-3.78(4H, s), 4.90-5.16(1H, m), 6.50-7.82(3H, m), 8.16 (1H, s) |
| 121 | H | OCH₃ | H | H | CH | Colorless powder (50.7%) 160-161.5° C. | (KBr) 3070, 2932, 1470, 1455, 1011, 996. | 1.17-2.70(7H, m), 2.21(3H, s), 2.83-3.17 (1H, m), 3.47(3H, s), 4.90-5.17(1H, m), 6.48-7.76(3H, m), 8.17(1H, s) |
| 122 | 3-CH₃ | OCH₂CF₃ | H | Na | CH | Colorless powder (77.6%) — | (KBr) 3420, 1580, 1472, 1454, 1376, 1290, 1264, 1166, 1090, 1016, 972, 744. | 1.00-3.60(6H, m), 4.40-4.96(3H, m), 6.70-7.08(3H, m), 7.33-7.65(2H, m), 8.26(1H, d, J=6Hz) |
| 123 | 3-CH₃ | SCH₂CH₂CH₃ | H | H | CH | Colorless powder (71.4%) 158-159° C. | (KBr) 2962, 2926, 1434, 1410, 1380, 1266, 999, 798, 744. | 0.80-1.05(3H, t, J=7Hz), 1.10-2.10(8H, m), 2.21-2.50(2H, t, J=8Hz), 2.44(3H, s), 2.53-2.93(1H, m), 3.40-3.71(1H, m), 4.98-5.18(1H, d, J=11Hz), 7.03-7.33(3H, m), 7.62-7.84(1H, m), 8.28(1H, s) |
| 124 | H | OCH₂CH₂OCH₃ | H | H | N | Brown amorphous powder (77.1%) 97-99° C. | (KBr) 2920, 1580, 1452, 1270, 1123, 1059. | 1.05-1.60(2H, m), 1.62-2.75(4H, m), 3.43 (3H, s), 3.62-3.90(2H, m), 3.95-4.28(2H, m), 4.50-4.72(1H, d, J=10Hz), 6.56-6.80 (1H, m), 7.07-7.30(1H, m), 7.80-8.52(3H, m) |
| 125 | 3-CH₃ | H | H | H | N | Yellow amorphous powder (42.4%) 99-102° C. | (KBr) 2926, 1404, 1269, 1050, 957, 909, 888, 804, 774. | 1.32-3.15(8H, m), 2.20(3H, s), 2.21(3H, s), 3.06-3.21(1H, m), 1.69(3H, m), 4.60-4.80(1H, d, J=10Hz), 7.15-7.36(1H, t), 8.03-8.16 (1H, d, J=7Hz), 8.16(1H, s), 8.43-8.60 (1H, d, J=6Hz) |
| 126 | 3-CH₃ | OCH₃ | H | H | N | Palely yellow powder (78.8%) 138-140° C. | (KBr) 2943, 1600, 1477, 1440, 1410, 1268, 1059, 817. | 1.30-2.75(7H, m), 2.19(3H, s), 3.06-3.21 (1H, m), 3.86-4.25(3H, t, J=12Hz), 5.30-6.70(2H, m), 7.13-7.40(1H, m), 8.00-8.28 (2H, m), 8.45-8.60(1H, d, J=5Hz) |
| 127 | 3-CH₃ | OCH₂CF₂CF₂H | H | H | N | Colorless powder (83.7%) 118-119° C. | (KBr) 2935, 1590, 1454, 1407, 1269, 1195, 1107, 1051. | 1.00-3.50(8H, m), 3.53(3H, s), 3.76(3H, s), 5.39(1H, d, J=10Hz), 6.51(1H, d, 6Hz), 7.13-7.53(2H, m), 7.58-8.00(2H, m) |
| 127 | H | OCH₃ | H | SO₂CH₃ | CH | Colorless powder (11.8%) 159-161° C. | (KBr) 2988, 1584, 1476, 1434, 1358, 1286, 1250, 1234, 1170, 1046, 974, 812, 772, 538, 518. | |

TABLE 5-continued
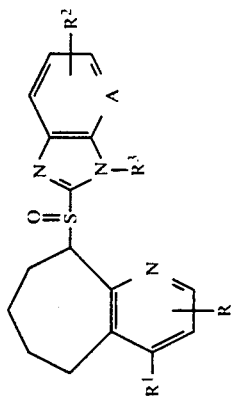
| Example No. | R | R¹ | R² | R³ | A | Melting point (yield) | IRνcm⁻¹ | NMR(CDCl₃)δ |
|---|---|---|---|---|---|---|---|---|
| | | | | | | | | 7.85(1H, d, J = 6Hz) |
In the table
*1 CDCl₃ — acetone-d₆
*2 CDCl₃ — DMSO-d₆

We claim:
1. A cycloheptenopyridine derivative of the formula

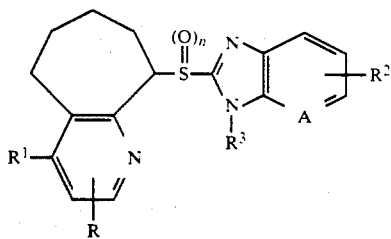

wherein R represents a hydrogen atom or lower alkyl group; $R^1$ represents a hydrogen atom, halogen atom, lower cycloalkoxy group, amido group, substituted phenoxy group, substituted benzyloxy group, lower alkoxy group optionally containing halogen atom(s), nitro group, hydroxyl group, lower alkenyloxy group, lower alkylthio group, or a group $-NR^4R^5$ wherein $R^4$ and $R^5$ may be the same or different and each represents a hydrogen atom or lower alkyl group, or $R^4$ and $R^5$ mutually combine together with the nitrogen atom adjacent thereto to form a 5- or 6- membered heterocyclic group; $R^2$ represents a hydrogen atom, halogen atom, lower alkyl group optionally containing a halogen atom, lower alkoxy group optionally containing a halogen atom, hydroxyl group, acyl group, lower alkoxycarbonyl group, nitro group or amino group; $R^3$ represents a hydrogen atom, a lower alkyl group, lower alkoxymethyl group, lower alkylcarbonyl group, lower alkoxycarbonyl group, carbamoyl group, lower alkylcarbamoyl group, lower alkylcarbonylmethyl group, lower alkoxycarbonylmethyl group, lower acyloxymethyl group, lower alkylsulfonyl group, or physiologically acceptable protective group eliminatable in an acid medium or under physiological conditions; n represents 0 or 1; and A represents a methine carbon or nitrogen atom or a pharmaceutically acceptable salt thereof.

2. An antiulcer composition which comprises an effective amount of a cycloheptenopyridine derivative of claim 1 or a pharmaceutically acceptable salt thereof, as an effective ingredient and a pharmaceutically acceptable carrier therefor.

* * * * *